(12) United States Patent
Gadek et al.

(10) Patent No.: US 6,762,190 B2
(45) Date of Patent: Jul. 13, 2004

(54) THIENYLALANINE DERIVATIVES AS INHIBITORS OF CELL ADHESION

(75) Inventors: Thomas Gadek, Oakland, CA (US); Jean-Francois Gourvest, Claye Souilly (FR); Anuschirwan Peyman, Kelkheim (DE); Jean-Marie Ruxer, Issy les Moulineaux (FR); Karl-Heinz Scheunemann, Liederbach (DE)

(73) Assignee: Aventis Pharma S.A. Deutschland GmbH Genentech, Inc. (DE)

( * ) Notice: Subject to any disclaimer, the term of this patent is extended or adjusted under 35 U.S.C. 154(b) by 10 days.

(21) Appl. No.: 10/169,612
(22) PCT Filed: Dec. 12, 2000
(86) PCT No.: PCT/EP00/12877
§ 371 (c)(1),
(2), (4) Date: Sep. 23, 2002
(87) PCT Pub. No.: WO01/44237
PCT Pub. Date: Jun. 21, 2001

(65) Prior Publication Data
US 2003/0105080 A1 Jun. 5, 2003

(30) Foreign Application Priority Data
Dec. 15, 1999 (GB) .............................. 99124971

(51) Int. Cl.[7] ..................... C07D 409/12; A61K 31/505
(52) U.S. Cl. ...................... 514/275; 514/218; 514/402; 540/553; 544/331; 548/332.5
(58) Field of Search .......................... 544/331; 514/275, 514/218, 402; 548/332.5; 540/553

(56) References Cited
FOREIGN PATENT DOCUMENTS

| EP | 0528587 | 2/1993 |
|---|---|---|
| EP | 0960882 | 12/1999 |
| WO | 9408577 | 4/1994 |
| WO | 9532710 | 12/1995 |
| WO | 9721726 | 6/1997 |
| WO | 9937621 | 7/1999 |

OTHER PUBLICATIONS

Ilvesaro, Cellular mechanisms of bone resorption, Attachment, Polarity And Communication Characteristics of Bone Cells, Academic Dissertation, University of Oulu, pp. 20–30, Apr. 2001.*

* cited by examiner

*Primary Examiner*—Deepak Rao
(74) *Attorney, Agent, or Firm*—Muserlian, Lucas, and Mercanti

(57) ABSTRACT

The present invention relates to compounds of formula (I), in which A, B, X, Y, $R^1$, $R^2$, $R^3$ and n have the meanings indicated in the claims. The compounds of formula (I) are valuable pharmacologically active compounds. They are vitronectin receptor antagonists and inhibitors of cell adhesion and are suitable for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for inhibiting bone resorption by osteoclasts and thus for treating and preventing osteoporosis, or for inhibiting undesired angiogenesis or proliferation of cells of the vascular smooth musculature. The invention furthermore relates to processes for the preparation of compounds of formula (I), their use, in particular as active ingredients in pharmaceuticals, and pharmaceutical compositions comprising them.

7 Claims, No Drawings

THIENYLALANINE DERIVATIVES AS INHIBITORS OF CELL ADHESION

This application is a 371 of PCT/EP00/12877 filed Dec. 12, 2000.

The present invention relates to compounds of the formula I,

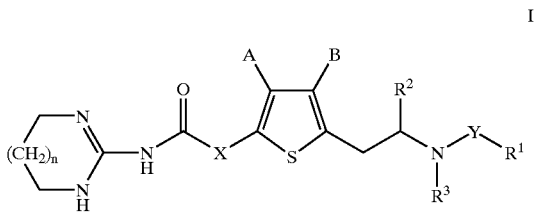

in which A, B, X, Y, $R^1$, $R^2$, $R^3$ and n have the meanings indicated below. The compounds of the formula I are valuable pharmacologically active compounds. They are vitronectin receptor antagonists and inhibitors of cell adhesion and are suitable for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for inhibiting bone resorption by osteoclasts and thus for treating and preventing osteoporosis, or for inhibiting undesired angiogenesis or proliferation of cells of the vascular smooth musculature. The invention furthermore relates to processes for the preparation of compounds of the formula I, their use, in particular as active ingredients in pharmaceuticals, and pharmaceutical compositions comprising them.

Human bones are subject to a constant dynamic renovation process comprising bone resorption and bone formation. These processes are controlled by types of cell specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodelling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry 31 (1996) 211).

Activated osteoclasts are polynuclear cells having a diameter of up to 400 µm, which remove bone matrix. Activated osteoclasts become attached to the surface of the bone matrix and secrete proteolytic enzymes and acids into the so-called "sealing zone", the region between their cell membrane and the bone matrix. The acidic environment and the proteases cause the destruction of the bone. The compounds of the formula I inhibit bone resorption by osteoclasts.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$, which is expressed on the osteoclast membrane, controls the process of attachment to the bones and bone resorption and thus contributes to osteoporosis. $\alpha_v\beta_3$ in this case binds to bone matrix proteins such as osteopontin, bone sialoprotein and thrombospontin which contain the tripeptide motif Arg-Gly-Asp (or RGD).

Horton and coworkers describe RGD peptides and an anti-vitronectin receptor antibody (23C6) which inhibit tooth destruction by osteoclasts and the migration of osteoclasts (Horton et al., Exp. Cell. Res. 195 (1991) 368). In J. Cell Biol. 111 (1990) 1713 Sato et al. describe echistatin, an RGD peptide from snake venom, as a potent inhibitor of bone resorption in a tissue culture and as an inhibitor of osteoclast adhesion to the bones. Fisher et al. (Endocrinology 132 (1993) 1411) and Yamamoto et al. (Endocrinology 139 (1998) 1411) were able to show in the rat that echistatin also inhibits bone resorption in vivo.

It was furthermore shown that the vitronectin receptor $\alpha_v\beta_3$ on human cells of the vascular smooth musculature of the aorta stimulates the migration of these cells into the neointima which finally leads to arteriosclerosis and restenosis after angioplasty (Brown et al., Cardiovascular Res. 28 (1994) 1815). Yue et al. (Pharmacology Reviews and Communications 10 (1998) 9) show the inhibition of neointima formation using an $\alpha_v\beta_3$ antagonist.

Brooks et al. (Cell 79 (1994) 1157) showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al., Annual Reports in Medicinal Chemistry 31 (1996) 191). The melanoma invasiveness correlated with this overexpression (Stracke et al., Encyclopedia of Cancer, volume III, 1855, Academic Press, 1997; Hillis et al., Clinical Science 91 (1996) 639). Carron et al. (Cancer Res. 58 (1998) 1930) describe the inhibition of tumor growth and the inhibition of hypercalcemia of malignancy using an $\alpha_v\beta_3$ antagonist.

Friedlander et al. (Science 270 (1995) 1500) describe anti-$\alpha_v\beta_3$ antibodies or $\alpha_v\beta_3$ antagonists which inhibit the bFGF-induced angiogenesis processes in the rat eye, a property which can be used therapeutically in the treatment of retinopathies and in the treatment of psoriasis. Storgard et al. (J. Clin. Invest. 103 (1999) 47) describe the use of $\alpha_v\beta_3$ antagonists in the treatment of arthritic diseases.

Influencing of the vitronectin receptor or of the interactions in which it is involved thus offers the possibility of influencing different disease states for whose therapy and prophylaxis there continues to be a need for suitable pharmaceutical active ingredients.

RGD peptides as inhibitors of bone resorption, angiogenesis and restenosis are described in WO-A-95/28426. EP-A-528586 and EP-A-528587 disclose aminoalkyl-substituted or heterocyclyl-substituted phenylalanine derivatives, and WO-A-95/32710 discloses aryl derivatives as inhibitors of bone resorption by osteoclasts. WO-A-99/32457 discloses carbamic ester derivatives, and WO-A-99/37621 discloses sulfonamides which are vitronectin receptor antagonists. Further vitronectin receptor antagonists are disclosed in WO-A-98/08840 and WO-A-98/18461. Thiophene derivatives exhibiting a fibrinogen receptor antagonistic activity are described in WO-A-94/08577. Thiophene derivatives as inhibitors of bone resorption are described in EP-A-960882 and U.S. Pat. No. 5,703,074. Further investigations have shown that the compounds of the formula I are particularly strong inhibitors of the vitronectin receptor and of bone resorption by osteoclasts.-

The present invention relates to compounds of the formula I,

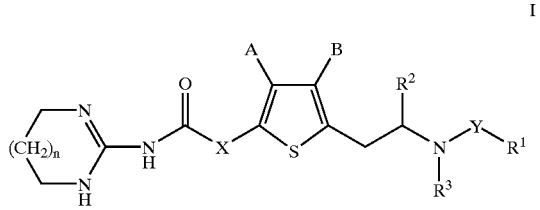

wherein

A and B which are independent of each other and are identical or different, are hydrogen, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, cyano, trifluoromethyl, nitro, hydroxycarbonyl-, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_5-C_{14})$-arylcarbonyl-, $(C_1-C_6)$-alkylaminocarbonyl-, $(C_1-C_6)$-alkoxy-$(C_1-C_6)$-alkoxy-, $(C_5-C_{14})$-aryl-$(C_1-C_8)$-alkylcarbonyl-, $(C_1-C_6)$-alkanoylamino-, $(C_1-C_6)$-alkylamino-, di-$((C_1-C_6)$-alkyl)amino-, $(C_1-C_6)$-alkylsulfonyl- or aminosulfonyl-, or the groups A and B bonded to the thiophene ring in the formula I together with the carbon atoms to which they are bonded form an aromatic or non-aromatic ring system that is fused to the thiophene ring;

X is $(C_3-C_6)$-alkanediyl, $(C_3-C_6)$-alkenediyl or $(C_3-C_6)$-alkynediyl, where in all these residues one carbon atom can be replaced by a heteroatom selected from the series consisting of nitrogen, oxygen and sulfur and where all these residues can be substituted by one or two identical or different substituents from the series consisting of hydroxy and A;

Y is a direct bond, —S(O)$_2$—, —C(O)—, —C(O)—O—, —S(O)$_2$—N(R$^{3'}$)— or —C(O)—N(R$^{3'}$)—, where the divalent residues representing Y are bonded to the group R$^1$ via the free bond on their right side;

R$^1$ is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl or $(C_5-C_{14})$-aryl-$(C_1-C_8)$-alkyl-, where the alkyl, cycloalkyl and aryl residues can be substituted one, two or three times by identical or different substituents from the series consisting of fluorine, chlorine, bromine, cyano, trifluoromethyl, nitro, hydroxycarbonyl-, $(C_1-C_6)$-alkyl, $(C_5-C_{14})$-aryl, $(C_5-C_{14})$-aryl-$(C_1-C_8)$-alkyl-, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di-$((C_1-C_6)$-alkyl)amino-, $(C_1-C_6)$-alkylsulfonyl-, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl-, $(C_5-C_{14})$-arylsulfonyl-, $(C_5-C_{14})$-aryl-$(C_1-C_8)$-alkylsulfonyl- and a residue of a saturated or partially unsaturated, monocyclic or polycyclic 3-membered to 14-membered ring which can contain one, two, three or four ring heteroatoms from the series consisting of nitrogen, oxygen and sulfur and which can be substituted by one or two identical or different substituents from the series consisting of A, =O and =S;

R$^2$ is —C(O)R$^4$, —C(S)R$^4$, —S(O)$_2$R$^4$, —P(O)R$^4$R$^{4'}$ or a residue of a saturated or unsaturated 4-membered to 8-membered heterocycle which contains one, two, three or four heteroatoms from the series consisting of nitrogen, oxygen and sulfur;

R$^3$ and R$^{3'}$ which are independent of each other and are identical or different, are hydrogen, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl or $(C_5-C_{14})$-aryl-$(C_1-C_8)$-alkyl-;

R$^4$ and R$^{4'}$ which are independent of each other and are identical or different are hydroxy, $(C_1-C_8)$-alkoxy, $(C_5-C_{14})$-aryl-$(C_1-C_8)$-alkoxy-, $(C_1-C_8)$-alkylcarbonyloxy-$(C_1-C_4)$-alkoxy-, $(C_5-C_{14})$-aryl-$(C_1-C_8)$-alkylcarbonyloxy-$(C_1-C_8)$-alkoxy- or —NR$^5$R$^{5'}$;

R$^5$ and R$^{5'}$ which are independent of each other and are identical or different are hydrogen, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl or $(C_5-C_{14})$-aryl-$(C_1-C_8)$-alkyl-, or R$^5$ and R$^{5'}$ together with the nitrogen atom to which they are bonded form a saturated or unsaturated 4-membered to 8-membered ring system which in addition to the nitrogen atom to which R$^5$ and R$^{5'}$ are bonded can contain one, two or three ring heteroatoms from the series consisting of nitrogen, oxygen and sulfur;

n is zero, one or two;

in all their stereoisomeric forms and mixtures thereof in all ratios, and their physiologically tolerable salts.

All substituents and residues which can occur several times in the compounds of the formula I, for example the residues A, but also all other residues to which this applies, can each independently of one another have the meanings indicated. They can all be identical or different. Likewise, heteroatoms in heterocyclic rings or substituents in residues which can be present several times can in each case independently of one another have the meanings indicated and can all be identical or different.

Alkyl residues can be straight-chain or branched and can be saturated or mono-unsaturated or poly-unsaturated. This also applies if they carry substituents or occur as substituents on other residues, for example in alkoxy residues, alkoxycarbonyl residues or arylalkyl residues. Substituted alkyl residues can be substituted in any suitable position. Examples of alkyl residues containing from 1 to 18 carbon atoms are methyl, ethyl, propyl, butyl, pentyl, hexyl, heptyl, octyl, nonyl, decyl, undecyl, dodecyl, tetradecyl, hexadecyl and octadecyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

Unsaturated alkyl residues can contain one or more, for example one, two or three, double bonds and/or triple bonds which can be in any suitable position. Of course, an unsaturated alkyl residue has to contain at least two carbon atoms. Examples of unsaturated alkyl residues are alkenyl residues such as vinyl, 1-propenyl, allyl, butenyl or 3-methyl-2-butenyl, or alkynyl residues such as ethynyl, 1-propynyl or propargyl. Alkyl residues can also be unsaturated when they are substituted. Preferably an unsaturated alkyl residue is mono-unsaturated and contains one double bond or triple bond.

The statements relating to alkyl residues correspondingly apply to divalent residues derived from saturated or unsaturated aliphatic hydrocarbons including the residues alkanediyl, alkenediyl and alkynediyl, and to residues which may be regarded as divalent or polyvalent alkyl residues, for example the alkyl moiety in a substituted alkyl residue like arylalkyl- or hydroxyalkyl-. Examples of alkanediyl residues are methylene, ethane-1,1-diyl, ethane-1,2-diyl, propane-1,2-diyl, propane-1,3-diyl, butane-1,4-diyl, pentane-1,5-diyl, 2,2-dimethylpropane-1,3-diyl, hexane-1,6-diyl. Examples of alkenediyl and alkynediyl residues are ethene-1,2-diyl, ethyne-1,2-diyl, prop-1-ene-1,3-diyl, prop-2-ene-1,3-diyl, prop-1-yne-1,3-diyl, prop-2-yne-1,3-diyl, but-1-ene-1,4-diyl, but-2-ene-1,4-diyl, but-3-ene-1,4-diyl, but-1-yne-1,4-diyl, but-2-yne-1,4-diyl, but-3-yne-1,4-diyl, pent-1-ene-1,5-diyl, pent-2-ene-1,5-diyl, pent-3-ene-1,5-diyl, pent-4-ene-1,5-diyl, pent-1-yne-1,5-diyl, pent-2-yne-1,5-diyl, pent-3-yne-1,5-diyl, pent-4-yne-1,5-diyl.

Cycloalkyl residues can be monocyclic or polycyclic, for example monocyclic, bicyclic or tricyclic, i.e., they can for example be monocycloalkyl residues, bicycloalkyl residues and tricycloalkyl residues, provided they have a suitable number of carbon atoms and the parent hydrocarbon systems are stable. A bicyclic or tricyclic cycloalkyl residue has to contain at least 4 carbon atoms. Preferably a bicyclic or tricyclic cycloalkyl residue contains at least 5 carbon atoms, more preferably at least 6 carbon atoms, and up to the number of carbon atoms specified in the respective definition. Thus, $(C_3-C_{14})$-cycloalkyl comprises but is not limited to, for example, $(C_3-C_{14})$-monocycloalkyl, $(C_6-C_{14})$-bicycloalkyl and $(C_6-C_{14})$-tricycloalkyl, and $(C_3-C_{12})$-cycloalkyl comprises but is not limited to, for example, $(C_3-C_{12})$-monocycloalkyl, $(C_6-C_{12})$-bicycloalkyl and $(C_6-C_{12})$-tricycloalkyl. Cycloalkyl residues can be saturated or contain one or more double bonds within the ring system. In particular they can be saturated or contain one double bond within the ring system. In unsaturated cycloalkyl residues the double bonds can be present in any suitable positions.

Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl which can also be substituted, for example by $(C_1-C_4)$-alkyl. Examples of substituted cycloalkyl residues which may be mentioned are 4-methylcyclohexyl and 2,3-dimethylcyclopentyl.

Bicycloalkyl residues and tricycloalkyl residues can likewise be unsubstituted or substituted in any desired suitable position, for example by one or more oxo groups and/or one or more identical or different $(C_1-C_4)$-alkyl groups, for example methyl or isopropyl groups, preferably methyl groups. The bond via which the bicyclic or the tricyclic residue is bonded can be located in any desired position in the molecule, and the residue can thus be bonded via a bridgehead atom or an atom in a bridge. The bond via which the residue is bonded can also be located in any desired stereochemical position, for example in an exo-position or an endo-position.

Examples of parent structures of bicyclic ring systems are norbornane (=bicyclo[2.2.1]heptane), bicyclo[2.2.2]octane and bicyclo[3.2.1]octane. An example of a system substituted by an oxo group is camphor (=1,7,7-trimethyl-2-oxobicyclo[2.2.1]heptane). Examples of parent structures of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane. A residue derived from adamantane can be 1-adamantyl or 2-adamantyl.

Unless specified otherwise, in each case the term $(C_5-C_{14})$-aryl is to be understood as comprising carbocyclic $(C_6-C_{14})$-aryl residues as well as heterocyclic $(C_5-C_{14})$-aryl residues (=$(C_5-C_{14})$-heteroaryl residues) in which one or more, for example one, two, three, four or five, of the 5 to 14 ring carbon atoms are replaced by heteroatoms such as nitrogen, oxygen or sulfur. Examples of carbocyclic aryl residues comprised by $(C_5-C_{14})$-aryl residues, and thus by $(C_6-C_{14})$-aryl residues, are phenyl, naphthyl such as 1-naphthyl or 2-naphthyl, biphenylyl such as 2-biphenylyl, 3-biphenylyl or 4-biphenylyl, anthryl or fluorenyl. Carbocyclic $(C_6-C_{12})$-aryl residues, in particular 1-naphthyl, 2-naphthyl and phenyl, are a preferred group of carbocyclic aryl residues. If not stated otherwise, all aryl residues, including phenyl residues, can be unsubstituted or substituted by one or more, preferably one, two or three, identical or different substituents. In particular substituted aryl residues can be substituted by identical or different residues from the series consisting of $(C_1-C_8)$-alkyl, in particular $(C_1-C_4)$-alkyl, $(C_1-C_8)$-alkoxy, in particular $(C_1-C_4)$-alkoxy, fluorine, chlorine and bromine, nitro, amino, $(C_1-C_4)$-alkylamino, di-(($C_1-C_4$)-alkyl)amino, trifluoromethyl, hydroxy, methylenedioxy, cyano, hydroxycarbonyl-, aminocarbonyl-, $(C_1-C_4)$-alkoxycarbonyl-, phenyl, phenoxy, benzyl, benzyloxy, tetrazolyl, $(R^9O)_2P(O)$— and $(R^9O)_2P(O)$—O— where $R^9$ is hydrogen, $(C_1-C_{10})$-alkyl, $(C_6-C_{14})$-aryl or $(C_6-C_{14})$-aryl-$(C_1-C_8)$-alkyl. Usually only up to two nitro groups can be present in the compounds of formula I, and similarly all other groups, substituents or heteroatoms mentioned in the definition of the compounds of formula I can only be present in the compounds of formula I in such positions and in such numbers and in such combinations that the resulting molecule is stable and does not exhibit characteristics that are not desired for the intended use.

In monosubstituted phenyl residues the substituent can be located in the 2-position, the 3-position or the 4-position, the 3-position and the 4-position being preferred. If phenyl is disubstituted, the substituents can be in 2,3-position, 2,4-position, 2,5-position, 2,6-position, 3,4-position or 3,5-position. Preferably in disubstituted phenyl residues the two substituents are located in 3,4-position relative to the linkage site. In trisubstituted phenyl residues, the substituents can be in 2,3,4-position, 2,3,5-position, 2,3,6-position, 2,4,5-position, 2,4,6-position or 3,4,5-position. Similarly, naphthyl residues and other aryl residues can be substituted in any desired position, for example a 1-naphthyl residue in the 2-, 3-, 4-, 5-, 6-, 7- or 8-position, a 2-naphthyl residue in the 1-, 3-, 4-, 5-, 6-, 7- or 8-position.

As mentioned, besides being carbocyclic aryl groups, $(C_5-C_{14})$-aryl groups can also be derived from monocyclic or polycyclic, for example monocyclic, bicyclic or tricyclic, aromatic ring systems in which one, two, three, four or five of the 5 to 14 ring carbon atoms are replaced by heteroatoms, in particular by identical or different heteroatoms from the series consisting of nitrogen, oxygen and sulfur. Just so, groups specifically designated as $(C_5-C_{14})$-heteroaryl groups, can be derived from monocyclic or polycyclic, for example monocyclic, bicyclic or tricyclic, aromatic ring systems in which one, two, three, four or five of the 5 to 14 ring carbon atoms are replaced by heteroatoms, in particular by identical or different heteroatoms from the series consisting of nitrogen, oxygen and sulfur. Examples of heterocyclic $(C_5-C_{14})$-aryl groups and $(C_5-C_{14})$-heteroaryl groups are pyridinyl like 2-pyridinyl, 3-pyridinyl and 4-pyridinyl, pyrrolyl like 2-pyrrolyl and 3-pyrrolyl, furyl like 2-furyl and 3-furyl, thienyl like 2-thienyl and 3-thienyl, imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolinyl, isoquinolinyl, quinoxalinyl, quinazolinyl, cinnolinyl, β-carbolinyl, or benzo-fused, cyclopenta-fused, cyclohexa-fused or cyclohepta-fused derivatives of these residues. The heterocyclic aromatic systems can be substituted in any suitable position by the substituents listed above with respect to carbocyclic aromatic systems. Heteroaryl residues and all other heterocyclic residues including saturated heterocyclic residues can be bonded via any suitable ring carbon atom and ring nitrogen atom.

In the series of heteroaryl groups, monocyclic or bicyclic aromatic ring systems which contain 1, 2 or 3 ring heteroatoms, in particular 1 or 2 ring heteroatoms, from the series consisting of nitrogen, oxygen and sulfur and which are unsubstituted or substituted by 1, 2 or 3 substituents from the series consisting of $(C_1-C_6)$-alkyl, $(C_1-C_6)$-alkoxy, fluorine, chlorine, nitro, amino, trifluoromethyl, hydroxy, $(C_1-C_4)$-alkoxycarbonyl-, phenyl, phenoxy, benzyloxy and benzyl, are preferred. Particularly preferred here are monocyclic or bicyclic aromatic 5-membered to 10-membered ring systems containing 1, 2 or 3 heteroatoms, in particular containing 1 or 2 ring heteroatoms, from the series consisting of nitrogen, oxygen and sulfur which are unsubstituted or substituted by 1 or 2 substituents from the series consisting of $(C_1-C_4)$-alkyl, $(C_1-C_4)$-alkoxy, phenyl, phenoxy, benzyl and benzyloxy. More particularly preferred are 5-membered or 6-membered monocyclic heteroaryl groups and 9-membered or 10-membered bicyclic heteroaryl groups containing 1 or 2, in particular 1, ring heteroatom from the series consisting of nitrogen, oxygen and sulfur which are unsubstituted or substituted as described before.

In addition to the above-mentioned heteroaryl groups, the following non-aromatic heterocycles may be mentioned as examples of saturated and unsaturated, including partially unsaturated, heterocyclic ring systems, provided that the specific example is in line with the definition of the respective group in the compounds of the formula I: aziridine, azetidine, tetrahydropyran, 1,4-dioxacyclohexane, morpholine, thiomorpholine, piperazine, perhydroazepine, piperidine, pyrrolidine, dihydroisoxazole, tetrahydroisoxazole, 1,3-dioxolane, 1,2-dithiolane, 2,3-dihydrofuran, 2,5-dihydrofuran, tetrahydrofuran, 2,3-dihydrothiophene, 2,5-dihydrothiophene, tetrahydrothiophene, 2-imidazoline, 3-imidazoline, 4-imidazoline, imidazolidine, 2-oxazoline, 3-oxazoline, 4-oxazoline, oxazolidine, 2-thiazoline, 3-thiazoline, 4-thiazoline, thiazolidine, 2H-thiopyran, 2H-pyran, 4H-pyran. In partially unsaturated ring systems for example one, two or three double bonds may be present within the ring system provided that the resulting ring system is non-aromatic. The above explanations with respect to heteroaryl residues, for example relating to substituents that may be present or attachment via any suitable position, correspondingly apply to the saturated and partially unsaturated ring systems.

The above statements relating to aryl residues including heteroaryl residues also correspondingly apply to the aryl moiety in groups like, for example, arylalkyl- including heteroarylalkyl-. Examples of arylalkyl- residues which in all cases can also carry in the aryl moiety the substituents listed above with respect to aryl groups, are benzyl, 1-phenylethyl-, 2-phenylethyl- or pyridinylmethyl-.

Optically active carbon atoms present in the compounds of the formula I can independently of one another have R configuration or S configuration. The compounds of the formula I can be present in the form of pure enantiomers or pure diastereomers or in the form of mixtures of enantiomers, for example in the form of racemates, or of mixtures of diastereomers. The present invention relates to all pure enantiomers and mixtures of enantiomers, as well as to pure diastereomers and mixtures of diastereomers. The invention comprises mixtures of two or of more than two stereoisomers of the formula I, and it comprises all ratios of stereoisomers in the mixtures. Compounds of the formula I containing respective structural units can also be present as E isomers or Z isomers (or trans isomers or cis isomers). The invention relates to all pure E isomers, pure Z isomers, pure cis isomers, pure trans isomers and to E/Z mixtures and cis/trans mixtures in all ratios. The invention also comprises all tautomeric forms of the compounds of the formula I. Diastereomers, including E/Z isomers, can be separated into the individual isomers by chromatography, for example. Racemates can be separated into the two enantiomers by customary methods like, for example, chromatography on chiral phases or resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example carboxylic acid groups, are, for example, alkali metal salts or alkaline earth metal salts such as, for example, sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine. Basic groups in the compounds of the formula I can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which simultaneously contain a basic group and an acidic group, for example a carboxyl group in addition to basic nitrogen atoms, can be present as zwitterions (or betaines or inner salts) which are likewise included by the present invention.

Salts of compounds of the formula I can be obtained by customary methods known to those skilled in the art, for example by combining a compound of the formula I with an inorganic or organic acid or base in a solvent or diluent, or from other salts by cation exchange or anion exchange. A subject of the present invention are also all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention moreover includes all solvates of compounds of the formula I, for example hydrates or adducts with alcohols, and also derivatives of the compounds of the formula I like esters, prodrugs and other physiologically tolerable derivatives, as well as active metabolites of the compounds of the formula I. A subject of the invention are in particular prodrugs of the compounds of the formula I which can be converted into compounds of the formula I under physiological conditions. More detailed information relating to prodrugs, i.e. chemically modified derivatives of the compounds of the formula I having properties which are improved in a desired manner, is found, for example, in Fleisher et al., Advanced Drug Delivery Reviews 19 (1996) 115; Design of Prodrugs, H. Bundgaard (ed.), Elsevier, 1985; or H. Bundgaard, Drugs of the Future 16 (1991) 443; which are all incorporated herein by reference. Suitable prodrugs for the compounds of the formula I are especially ester prodrugs and amide prodrugs of carboxylic acid groups, in particular of a COOH group representing $R^2$, for example alkyl esters, and also acyl prodrugs and carbamate prodrugs of acylatable nitrogen-containing groups such as amino groups or the diazacycloalkene ring depicted in the formula I. In the acyl prodrugs or carbamate prodrugs, one or more, for example one or two, hydrogen atoms on nitrogen atoms in such groups are replaced by an acyl group or a carbamate group. Suitable acyl groups and carbamate groups for the acyl prodrugs and carbamate prodrugs are, for example, the groups $R^{10}$—C(O)— and $R^{11}$O—C(O)—, in which $R^{10}$ is hydrogen, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl or $(C_5-C_{14})$-aryl-$(C_1-C_8)$-alkyl-, and in which $R^{11}$ has the meanings indicated for $R^{10}$ with the exception of hydrogen.

In case the groups A and B bonded to the thiophene ring in the formula I together with the carbon atoms to which they are bonded form an aromatic or non-aromatic ring system fused to the thiophene ring, said fused aromatic or non-aromatic ring system preferably is a carbocyclic ring like a benzo ring or a 5-membered, 6-membered or 7-membered cycloalkeno ring, particularly preferably a benzo ring, i.e., preferably in such case the thiophene ring in the formula I is replaced by a benzo[c]thiophene ring, a 5,6-dihydro-4H-cyclopenta[c]thiophene ring, 4,5,6,7-tetrahydrobenzo[c]thiophene ring or a 5,6,7,8-tetrahydro-4H-cyclohepta[c]thiophene ring.

The groups A preferably independently of each other denote hydrogen or $(C_1-C_6)$-alkyl, more preferably hydrogen or $(C_1-C_4)$-alkyl, particularly preferably hydrogen. The group B preferably denotes hydrogen or $(C_1-C_6)$-alkyl, more preferably hydrogen or $(C_1-C_4)$-alkyl, particularly preferably hydrogen.

The divalent residue X preferably is $(C_3-C_6)$-alkanediyl, $(C_3-C_6)$-alkenediyl or $(C_3-C_6)$-alkynediyl, more preferably $(C_3-C_6)$-alkanediyl or $(C_3-C_6)$-alkenediyl, particularly preferably $(C_3-C_6)$-alkanediyl, where in all these preferred residues no carbon atom is replaced by a heteroatom. Preferably the $(C_3-C_6)$ unit in a residue representing X is a $(C_4-C_5)$ unit, more preferably a $C_4$ unit. In case X is an alkenediyl or alkynediyl residue the double bond or triple bond, respectively, is preferably located between the carbon atom in X bonded to the thiophene ring and the adjacent carbon in the chain.

The divalent residue Y preferably is —S(O)$_2$— or —C(O)—O—, where the residue —C(O)—O— is bonded to the group $R^1$ via the free valence on the oxygen atom.

In case a residue representing $R^1$ carries as a substituent a residue of a saturated or partially unsaturated, monocyclic or polycyclic 3-membered to 14-membered ring, that substituent can be derived from a ring containing 3, 4, 5, 6, 7, 8, 9, 10, 11, 12, 13 or 14 ring atoms which ring can be a carbocyclic ring, i.e. a saturated or partially unsaturated cycloalkane, or a heterocyclic ring and preferably is monocyclic, bicyclic or tricyclic. Preferably such a substituent is derived from a 3-membered to 7-membered saturated or partially unsaturated ring which can contain one or two ring heteroatoms from the series consisting of nitrogen, oxygen and sulfur and which can be substituted by one or two identical or different substituents from the series consisting of A, =O and =S. The residue $R^1$ preferably is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl including carbocyclic $(C_6-C_{14})$-aryl and $(C_5-C_{14})$-heteroaryl, or $(C_5-C_{14})$-aryl-$(C_1-C_8)$-alkyl-including carbocyclic $(C_6-C_{14})$-aryl-$(C_1-C_8)$-alkyl- and $(C_5-C_{14})$-heteroaryl-$(C_1-C_8)$-alkyl-, where the alkyl, cycloalkyl and aryl residues including carbocyclic aryl residues and heteroaryl residues are unsubstituted or substituted one, two or three times by identical or different substituents from the series consisting of fluorine, chlorine, bromine, cyano, trifluoromethyl, $(C_1-C_6)$-alkyl, $(C_5-C_{14})$-aryl and $(C_1-C_6)$-alkoxy. More preferably $R^1$ is $(C_1-C_8)$-alkyl, bicyclic or tricyclic $(C_9-C_{12})$-cycloalkyl, bicyclic or tricyclic $(C_9-C_{12})$-cycloalkyl-$(C_1-C_4)$-alkyl-, carbocyclic $(C_6-C_{12})$-aryl or carbocyclic $(C_6-C_{12})$-aryl-$(C_1-C_4)$-alkyl-, where the $(C_1-C_8)$-alkyl, cycloalkyl and aryl residues are unsubstituted or substituted one, two or three times by identical or different substituents from the series consisting of fluorine, chlorine, bromine, cyano, trifluoromethyl, $(C_1-C_6)$-alkyl and $(C_1-C_6)$-alkoxy.

In case the group $R^2$ denotes the residue of a 4-membered to 8-membered saturated or unsaturated heterocycle said heterocycle may contain 4, 5, 6, 7 or 8 ring atoms. Examples of suitable heterocyclic residues are tetrazolyl, imidazolyl, pyrazolyl, oxazolyl or thiadiazolyl. An unsaturated heterocycle may be partially unsaturated or aromatic. Preferably $R^2$ denotes —C(O)$R^4$.

$R^3$ and $R^{3'}$ preferably are independently of each other hydrogen, $(C_1-C_6)$-alkyl or $(C_5-C_{14})$-aryl-$(C_1-C_8)$-alkyl-, more preferably hydrogen or $(C_1-C_4)$-alkyl, particularly preferably hydrogen.

$R^4$ and $R^{4'}$ preferably independently of each other are hydroxy, $(C_1-C_8)$-alkoxy, $(C_1-C_8)$-alkylcarbonyloxy-$(C_1-C_4)$-alkoxy- or —NR$^5$R$^{5'}$, more preferably hydroxy, $(C_1-C_6)$-alkoxy or —NR$^5$R$^{5'}$, particularly preferably hydroxy or $(C_1-C_5)$-alkoxy.

In case $R^5$ and $R^{5'}$ together with the nitrogen atom to which they are bonded form a 4-membered to 8-membered ring system said ring system can contain 4, 5, 6, 7 or 8 ring atoms and preferably is monocyclic. Preferably said ring system is saturated. Examples of suitable ring systems are pyrrolidine, piperidine, morpholine, thiomorpholine and piperazine. $R^5$ and $R^{5'}$ preferably are independently of each other hydrogen, $(C_1-C_6)$-alkyl or $(C_5-C_{14})$-aryl-$(C_1-C_8)$-alkyl-, or $R^5$ and $R^{5'}$ together with the nitrogen atom to which they are bonded form a 4-membered to 6-membered ring system which in addition to the nitrogen atom to which $R^5$ and $R^{5'}$ are bonded can contain one, two or three ring heteroatoms from the series consisting of nitrogen, oxygen and sulfur and which is unsaturated or saturated, where preferably said ring system in addition to the nitrogen atom to which $R^5$ and $R^{5'}$ are bonded contains zero or one heteroatom from the series consisting of nitrogen, oxygen and sulfur and is saturated. More preferably $R^5$ and $R^{5'}$ are independently of each other hydrogen or $(C_1-C_4)$-alkyl, particularly preferably hydrogen.

n preferably is zero or one, more preferably one. I. e., the residue of the diazacycloalkene ring depicted in the formula I preferably is 4,5-dihydro-1H-imidazol-2-yl or 1,4,5,6-tetrahydropyrimidin-2-yl, more preferably 1,4,5,6-tetrahydropyrimidin-2-yl.

In the compounds of formula I according to the invention the various groups, residues and numbers can independently of one another have the above preferred definitions or can have one or more of the specific denotations given in their respective definitions or in the general explanations on the respective groups and residues. Preferred compounds of the present invention are those compounds of the formula I in which one or more of the residues have preferred definitions, or have one or more specific denotations given in their respective definitions or general explanations, all combinations of such preferred definitions and specific denotations being a subject of the present invention.

A group of preferred compounds is formed, for example, by compounds of the formula I in which the groups A and B bonded to the thiophene ring in the formula I are hydrogen;

X is $(C_3-C_6)$-alkanediyl, $(C_3-C_6)$-alkenediyl or $(C_3-C_6)$-alkynediyl;

Y is —S(O)$_2$— or —C(O)—O—;

$R^1$ is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl or $(C_5-C_{14})$-aryl-$(C_1-C_8)$-alkyl-, where the alkyl, cycloalkyl and aryl residues can be substituted one, two or three times by identical or different substituents from the series consisting of fluorine, chlorine, bromine, cyano, trifluoromethyl, nitro, hydroxycarbonyl-, $(C_1-C_6)$-alkyl, $(C_5-C_{14})$-aryl, $(C_5-C_{14})$-aryl-$(C_1-C_8)$-alkyl-, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di-($(C_1-C_6)$-alkyl)amino-, $(C_1-C_6)$-alkylsulfonyl-, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl-, $(C_5-C_{14})$-arylsulfonyl-, $(C_5-C_{14})$-aryl-$(C_1-C_8)$-alkylsulfonyl- and a residue of a saturated or partially unsaturated, monocyclic or polycyclic 3-membered to 14-membered ring which can contain one, two, three or four ring heteroatoms from the series consisting of nitrogen, oxygen and sulfur and which can be substituted by one or two identical or different substituents from the series consisting of $(C_1-C_{18})$-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, fluorine, chlorine, bromine, cyano, trifluoromethyl, nitro, hydroxycarbonyl-, ($C_1$–$C_6$)-alkoxy, ($C_1$–$C_6$)-alkoxy-($C_1$–$C_6$)-alkyl-, ($C_1$–$C_6$)-alkoxycarbonyl-, ($C_1$–$C_6$)-alkylcarbonyl-, ($C_5$–$C_{14}$)-arylcarbonyl-, ($C_1$–$C_6$)-alkylaminocarbonyl-, ($C_1$–$C_6$)-alkoxy-($C_1$–$C_6$)-alkoxy-, ($C_5$–$C_{14}$)-aryl-($C_1$–$C_8$)-alkylcarbonyl-, ($C_1$–$C_6$)-alkanoylamino-, ($C_1$–$C_6$)-alkylamino-, di-(($C_1$–$C_6$)-alkyl)amino-, ($C_1$–$C_6$)-alkylsulfonyl-, aminosulfonyl-, =O and =S;

$R^2$ is —C(O)$R^4$;

$R^3$ is hydrogen, ($C_1$–$C_6$)-alkyl or ($C_5$–$C_{14}$)-aryl-($C_1$–$C_8$)-alkyl-;

$R^4$ is hydroxy, ($C_1$–$C_8$)-alkoxy, ($C_1$–$C_8$)-alkylcarbonyloxy-($C_1$–$C_4$)-alkoxy- or —N$R^5 R^{5'}$;

$R^5$ and $R^{5'}$ which are independent of each other and are identical or different are hydrogen, ($C_1$–$C_6$)-alkyl or ($C_5$–$C_{14}$)-aryl-($C_1$–$C_8$)-alkyl-, or $R^5$ and $R^{5'}$ together with the nitrogen atom to which they are bonded form a 4-membered to 8-membered ring system which in addition to the nitrogen atom to which $R^5$ and $R^{5'}$ are bonded can contain one, two or three ring heteroatoms from the series consisting of nitrogen, oxygen and sulfur and which is unsaturated or saturated;

n is zero or one;

in all their stereoisomeric forms and mixtures thereof in all ratios, and their physiologically tolerable salts.

A group of more preferred compounds is formed, for example, by compounds of the formula I in which the groups A and B bonded to the thiophene ring in the formula I are hydrogen;

X is ($C_3$–$C_6$)-alkanediyl, ($C_3$–$C_6$)-alkenediyl or ($C_3$–$C_6$)-alkynediyl;

Y is —S(O)$_2$— or —C(O)—O—;

$R^1$ is ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl or ($C_5$–$C_{14}$)-aryl-($C_1$–$C_8$)-alkyl-, where the alkyl, cycloalkyl and aryl residues can be substituted one, two or three times by identical or different substituents from the series consisting of fluorine, chlorine, bromine, cyano, trifluoromethyl, ($C_1$–$C_6$)-alkyl, ($C_5$–$C_{14}$)-aryl and ($C_1$–$C_6$)-alkoxy;

$R^2$ is —C(O)$R^4$;

$R^3$ is hydrogen or ($C_1$–$C_4$)-alkyl;

$R^4$ is hydroxy, ($C_1$–$C_6$)-alkoxy or —N$R^5 R^{5'}$;

$R^5$ and $R^{5'}$ which are independent of each other and are identical or different are hydrogen or ($C_1$–$C_4$)-alkyl;

n is zero or one;

in all their stereoisomeric forms and mixtures thereof in all ratios, and their physiologically tolerable salts.

A group of particularly preferred compounds is formed, for example, by compounds of the formula I in which the groups A and B bonded to the thiophene ring in the formula I are hydrogen;

X is ($C_3$–$C_6$)-alkanediyl, ($C_3$–$C_6$)-alkenediyl or ($C_3$–$C_6$)-alkynediyl;

Y is —S(O)$_2$— or —C(O)—O—;

$R^1$ is ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl or ($C_5$–$C_{14}$)-aryl-($C_1$–$C_8$)-alkyl-, where the alkyl, cycloalkyl and aryl residues can be substituted one, two or three times by identical or different substituents from the series consisting of fluorine, chlorine, bromine, cyano, trifluoromethyl, ($C_1$–$C_6$)-alkyl, ($C_5$–$C_{14}$)-aryl and ($C_1$–$C_6$)-alkoxy;

$R^2$ is —C(O)$R^4$;

$R^3$ is hydrogen;

$R^4$ is hydroxy or ($C_1$–$C_5$)-alkoxy;

n is one;

in all their stereoisomeric forms and mixtures thereof in all ratios, and their physiologically tolerable salts.

Further, preferred compounds of the present invention are those compounds in which the asymmetric carbon atom in the formula I to which the groups $R^2$ and $R^1$—Y—N($R^3$)— are bonded, has S configuration, and their physiologically tolerable salts.

The present invention also relates to processes of preparation by which the compounds of the formula I are obtainable and which comprise carrying out one or more of the synthesis steps described below. The compounds of the formula I can generally be prepared, for example in the course of a convergent synthesis, by linkage of two or more fragments which can be derived retrosynthetically from the formula I. In the course of the preparation of the compounds of the formula I it can generally be advantageous or necessary to introduce functional groups which could lead to undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991). As examples of precursor groups nitro groups and cyano groups may be mentioned which can later be converted by reduction, for example by catalytic hydrogenation, into amino groups and aminomethyl groups, respectively. Examples of protective groups are mentioned in the following.

For example, for the preparation of a compound of the formula I a building block of the formula II,

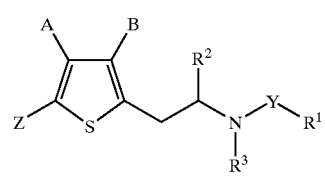

II in which Z is a suitable leaving group like chlorine, bromine or iodine, can be used. In the compounds of the formula II the groups A, B, Y, $R^1$, $R^2$ and $R^3$ are as defined above for the compounds of the formula I but functional groups can optionally also be present in the form of precursor groups or can be protected by protective groups. In particular, for example, a group $R^2$ in a compound of the formula I denoting hydroxycarbonyl-(—COOH) is preferably present in a starting compound of the formula II as an ester like a tert-butyl ester or a methyl ester or an ethyl ester group. Furthermore, in particular in the compounds of the formula II the groups $R^1$ and Y taken together, i.e. the group $R^1$—Y—, can denote a hydrogen atom or, preferably, an amino protecting group, for example a benzyloxycarbonyl group, i.e., the group $R^1$—Y—N($R^3$)— in the compounds of the formula II can also be the group $R^3$NH— or, preferably, a protected form thereof.

A compound of the formula II is reacted with a compound of the formula III,

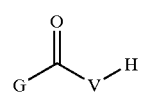

III in which G is hydroxy or a protected hydroxy group of a carboxylic acid group or a nucleophilically substitutable leaving group. I. e., the group G—CO— in the compounds of the formula III is a carboxylic acid group or a protected carboxylic acid group or an activated derivative of a carboxylic acid group. The divalent residue V in the compounds of the formula III is a divalent $(C_3-C_6)$-alkenediyl or $(C_3-C_6)$-alkynediyl residue containing a terminal double bond or a triple bond in the terminal position that carries the hydrogen atom depicted in formula III, where in the residues V one carbon atom can be replaced by a heteroatom selected from the series consisting of nitrogen, oxygen and sulfur and where the residues V can be substituted by one or two identical or different substituents from the series consisting of hydroxy and A, and where functional groups can optionally also be present in the form of precursor groups or can be protected by protective groups.

The coupling reaction of the compounds of the formulae II and III is carried out in the presence of a metal catalyst like, for example, a palladium or copper catalyst under conditions which are known to those skilled in the art and which are described, for example, in J. March, Advanced Organic Chemistry, Fourth Edition, J. Wiley, 1992 for such metal-catalyzed coupling reactions of suitably substituted arenes like haloarenes with alkenes or alkynes. The metals used as catalysts can be employed in the form of complexes or salts, if appropriate with the addition of triarylphosphines. For example, palladium(II) acetate can be used as a catalyst. The reaction of the compounds of formulae II and III is usually carried out in an inert organic solvent or diluent, for example dichloromethane (DCM), chloroform, tetrahydrofuran (THF), diethyl ether, n-heptane, n-hexane, n-pentane, cyclohexane, diisopropyl ether, methyl tert-butyl ether, acetonitrile, dimethylformamide (DMF), dimethylsulfoxide (DMSO), dioxane, toluene, benzene, ethyl acetate or a mixture of these solvents, if appropriate with addition of a base such as, for example, potassium carbonate, potassium tert-butoxide or tributylamine, and/or addition of a phase transfer catalyst such as, for example, tetrabutylammonium chloride, at temperatures from about 0° C. to about 180° C.

From the compounds of the formulae II and III a compound of the formula IV

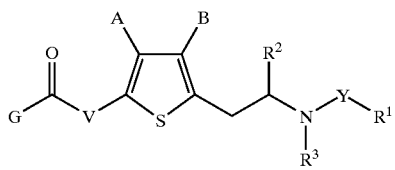

IV is obtained in which A, B, G, V, Y, $R^1$, $R^2$ and $R^3$ are defined as for formulae II and III. If a compound of the formula I is to be synthesized in which X is a saturated alkanediyl residue the double bond or triple bond in the group V in the compound of the formula IV is converted to a single bond, for example by catalytic hydrogenation in the presence of a catalyst such as palladium on charcoal in a suitable solvent such as methanol, ethanol or acetic acid. If a compound of the formula I is to be synthesized in which a double or triple bond in the group X is present in a position different from the position adjacent to the thiophene ring which results in the above synthesis of the compound of the formula IV, the double bond or triple bond can be shifted in a prototropic rearrangement reaction, for example in the presence of a base, where mixtures of isomers that may result can be separated, for example, by HPLC. A double or triple bond in the group X in another position than that adjacent to the thiophene ring can also be introduced, for example, by a dehydration or dehydrohalogenation reaction performed with a compound which contains a hydroxy substituent or one or two halogen substituents in the group V. Compounds of the formula IV themselves and compounds of the formula IV in which the group V has been modified are together represented by the formula V,

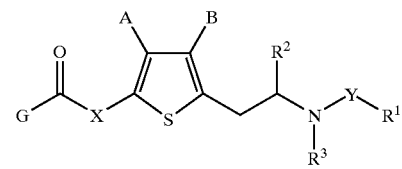

V in which A, B, G, Y, $R^1$, $R^2$ and $R^3$ are defined as for the formulae II and III and the group X is as defined above for the compounds of the formula I but where functional groups in X can optionally also be present in the form of precursor groups or can be protected by protective groups.

If the group $R^1$—Y— in a compound of the formula V stands for an amino protecting group, for example benzyloxycarbonyl, the compound of the formula V is converted into a compound of the formula VI by deprotection using methods well known to those skilled in the art, for example catalytic hydrogenation in the case of a benzyloxycarbonyl group. In the compounds of the formula VI A, B, G, X, $R^2$ and $R^3$ are defined as for the formulae II and III.

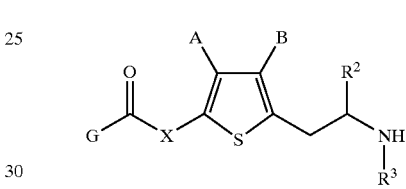

VI

If it is desired to prepare a compound of the formula VI in which X denotes a saturated alkanediyl residue, the conversion of an unsaturated alkenediyl or alkynediyl residue representing the group V in a compound of the formula IV into a saturated alkanediyl residue and the deprotection of a benzyloxycarbonyl-protected amino group can favorably be carried out simultaneously by catalytic hydrogenation. Moreover, in case the group G denotes benzyloxy and it is desired for the further synthetic procedure to prepare the respective free carboxylic acid of the formula VII,

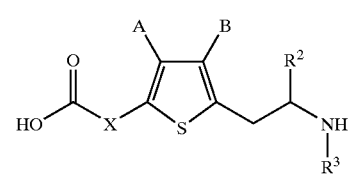

VII the cleavage of the benzyl ester to give the carboxylic acid, the deprotection of the benzyloxycarbonyl-protected amino group and the conversion of an alkenediyl or alkynediyl linker into an alkanediyl linker can all be carried simultaneously in a single step by catalytic hydrogenation. In the compounds of the formula VII A, B, X, $R^2$ and $R^3$ are defined as for the formula V. If the group G in a compound of the formula V or VI is another protecting group than benzyloxy and it is desired to prepare the free carboxylic acid of the formula VII, deprotection can be achieved by other well-known standard methods, for example by cleavage with trifluoroacetic acid in case G is tert-butoxy or by alkaline hydrolysis, for example with lithium hydroxide, in case G is methoxy or ethoxy.

Depending on the synthetic strategy, instead of converting a compound of the formula VI in which G is a protective group into the free carboxylic acid of the formula VII, it can also be favorable to convert a compound of the formula V in which G is a protective group into the free carboxylic acid of the formula VIII,

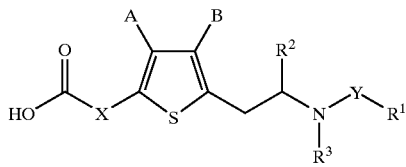

VIII in which A, B, X, Y, $R^1$, $R^2$ and $R^3$ are as defined for the formula V, for example by catalytic hydrogenation in case G is benzyloxy, or by cleavage with trifluoroacetic acid in case G is tert-butoxy, or by alkaline hydrolysis in case G is methoxy or ethoxy. By the choice of protecting groups it is possible to achieve a conversion only in that part of the molecules where it is desired in the respective synthesis step.

Into the compounds of the formulae VI or VII the group $R^1$—Y— in which $R^1$ and Y are defined as for the compounds of the formula I, can be introduced under standard conditions for the alkylation, acylation or sulfonylation of amines or their conversion into carbamates, sulfamides or ureas, for example by reaction with a compound of the formula IX,

L—Y—$R^1$      IX in which Y and $R^1$ are defined as above for the compounds of the formula I and L is a suitable nucleophilically substitutable leaving group, thus obtaining compounds of the formulae V or VIII in which $R^1$ and Y are defined as for the compounds of the formula I and A, B, G, X, $R^2$ and $R^3$ are defined as for the compounds of the formulae V and VIII. L can, for example, be chlorine, bromine, $R^1$—C(O)—O—, $R^1$—S(O)$_2$—O—, aryloxy, succinimidyloxy, etc. and the compounds of the formula IX can, for example, be chlorides and bromides including carboxylic acid chlorides and bromides, sulfonic acid chlorides and bromides and chloroformic acid derivatives, carboxylic acid anhydrides and sulfonic acid anhydrides, N-acyloxysuccinimides, or active esters of carboxylic acids like aryl esters such as pentafluorophenyl esters.

For the introduction of the diazacycloalkenylamino moiety a compound of the formulae V or VIII or a compound in which the carboxylic acid function therein is present as, or has been converted into, a suitable derivative, for example an ester, is coupled with a compound of the formula X,

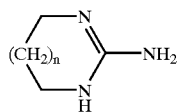

X in which the number n is defined as for the compounds of the formula I. For performing such a coupling reaction the carboxylic acid function in a compound of the formulae V or VIII is usually first activated, for example by one of the various methods used for peptide couplings which are well known to those skilled in the art. Examples of suitable activation agents are O-((cyano(ethoxycarbonyl)methylene) amino)-1,1,3,3-tetramethyluronium tetrafluoroborate (TOTU), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU) or carbodiimides like dicyclohexylcarbodiimide or diisopropylcarbodiimide. The activation of the carboxylic acid function may also favorably be carried, for example, by conversion of the carboxylic acid group into the pentafluorophenyl ester using dicyclohexylcarbodiimide and pentafluorophenol. The activation and the subsequent reaction with the compound of the formula X are usually carried in the presence of an inert solvent or diluent, for example DCM, chloroform, THF, diethyl ether, n-heptane, n-hexane, n-pentane, cyclohexane, diisopropyl ether, methyl tert-butyl ether, acetonitrile, DMF, DMSO, dioxane, toluene, benzene, ethyl acetate or a mixture of these solvents, if appropriate with addition of a base such as, for example, potassium tert-butoxide or tributylamine. The resulting product is a compound of the formula I in which A, B, X, Y, $R^1$, $R^2$, $R^3$ and n are defined as above for the compounds of the formula I but in which functional groups can also be present in the form of precursor groups or can be protected by protective groups. If still any protective groups or precursor groups are present they are then removed by known methods (see Greene and Wuts, Protective Groups in Organic Synthesis, Wiley, 1991), or converted in the desired final groups, respectively. If, for example, $R^2$ in the coupling product is a carboxylic acid group protected as tert-butyl ester and the free carboxylic acid is to be prepared as the final compound the protective group can be removed by reaction with trifluoroacetic acid. If desired, with the obtained compounds further reactions can then be carried out by standard processes, for example acylation reactions or esterification reactions, or the compounds can be converted into physiologically tolerable salts or prodrugs by standard processes known to those skilled in the art.

The starting compounds of the formulae II, III and IX which are linked to give the compounds of the formula I, are commercially available or can be prepared by or analogously to processes described below or in the literature.

The compounds of the formula I are valuable pharmacologically active compounds which are suitable, for example, for the therapy and prophylaxis of bone disorders, tumor diseases, cardiovascular disorders or inflammatory conditions. The compounds of the formula I and their physiologically tolerable salts and their prodrugs can be administered to animals, preferably to mammals, and in particular to humans, as pharmaceuticals for therapy or prophylaxis. They can be administered on their own or in mixtures with one another or in the form of pharmaceutical compositions which permit enteral or parenteral administration and which, as active constituent, contain an efficacious dose of at least one compound of the formula I and/or its physiologically tolerable salts and/or its prodrugs in addition to a pharmaceutically acceptable carrier.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs for the therapy and prophylaxis of these diseases and to methods for such therapy and prophylaxis. The present invention furthermore relates to pharmaceutical compositions (or pharmaceutical preparations) which contain an efficacious dose of at least one compound of the formula I and/or its physiologically tolerable salts and/or its prodrugs and a pharmaceutically acceptable carrier, i.e. one or more pharmaceutically acceptable carrier substances and/or additives.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions, emulsions or tinctures, or in other ways, for example in the form of aerosols or nasal sprays.

The pharmaceutical compositions according to the invention are prepared in a manner known per se and familiar to those skilled in the art, one or more compound(s) of the formula I and/or its (their) physiologically tolerable salts and/or its (their) prodrugs being mixed with one or more pharmaceutically acceptable inert inorganic and/or organic carrier substances and/or additives and, if desired, one or more other pharmaceutically active compounds, and being brought into a suitable administration form and dosage form that can be used in human or veterinary medicine. For the production of pills, tablets, coated tablets and hard gelatin capsules it is possible to use, for example, lactose, corn starch or derivatives thereof, talc, stearic acid or its salts, etc. Carriers for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical compositions normally contain about 0.5 to 90% by weight of the compounds of the formula I and/or their physiologically tolerable salts and/or their prodrugs. The amount of the active ingredient of the formula I and/or its physiologically tolerable salts and/or its prodrugs in the pharmaceutical compositions normally is from about 0.2 mg to about 1000 mg, preferably from about 1 mg to about 500 mg.

In addition to the active ingredients of the formula I and/or its physiologically tolerable salts and/or its prodrugs and carriers, the pharmaceutical compositions can contain additives (or auxiliary substances) such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and inhibitors of cell adhesion. They have, for example, the ability to inhibit the binding of osteoclasts to the bone surface and thereby inhibit bone resorption by osteoclasts. The action of the compounds of the formula I can be demonstrated, for example, in an assay in which the inhibition of the binding of the isolated vitronectin receptor or of cells which contain the vitronectin receptor to a ligand of the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compounds of the formula I and their physiologically tolerable salts and their prodrugs are therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with agents like bisphosphonates, estrogens, estrogen/progesterone, estrogen agonists/ antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical composition, for example tablets, capsules or granules, or can be present in two or more separate pharmaceutical compositions which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical compositions which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a pharmaceutically acceptable carrier. The above explanations on pharmaceutical compositions correspondingly apply to such pharmaceutical combination compositions.

Apart from use as inhibitors of bone resorption by osteoclasts, the compounds of the formula I and their physiologically tolerable salts and their prodrugs can be used, for example, as inhibitors of tumor growth and tumor metastasis, as antiinflammatories, for the therapy or prophylaxis of rheumatoid arthritis, for the therapy of psoriasis, for the therapy or prophylaxis of cardiovascular disorders such as arteriosclerosis or restenoses, for the therapy or prophylaxis of nephropathies or retinopathies such as, for example, diabetic retinopathy, or for the reduction of cell proliferation. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer, Academic Press, 1997 which is incorporated herein by reference. All the above statements relating to the use of the compounds of formula I in combination with conventional osteoporosis therapy like, for example, possible modes of administration and pharmaceutical combination compositions, correspondingly apply to the use of the compounds of formula I in combination with conventional cancer therapy.

When using the compounds of the formula I, the dose can vary within wide limits and, as is customary, is to be suited to the individual conditions in each individual case. It depends, for example, on the compound employed, on the nature and severity of the disease to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0.1 to about 5 mg/kg, to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Apart from use as pharmaceutical active ingredients, the compounds of the formula I can also be used as vehicles or carriers of other active ingredients in order to transport the active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag which is incorporated herein by reference). The active ingredients to be transported are in particular those which can be used for the treatment of the above-mentioned diseases.

The compounds of the formula I and their salts can furthermore be employed for diagnostic purposes, for example in in vitro diagnoses, and as auxiliaries in biochemical investigations in which blocking of the vitronectin receptor or influencing of cell-cell or cell-matrix interactions is desired. They can furthermore be used as synthesis intermediates for the preparation of other compounds, in particular of other pharmaceutical active ingredients, which are obtainable from the compounds of the formula I, for example by introduction of substituents or modification of functional groups.

EXAMPLES

Abbreviations

| AcOH | acetic acid |
| DCM | dichloromethane |
| DMF | N,N-dimethylformamide |
| EE | ethyl acetate |
| MeOH | methanol |
| TFA | trifluoroacetic acid |
| THF | tetrahydrofuran |

Example 1

(2S)-2-(Naphthalene-1-sulfonylamino)-3-(5-(4-(1,4,5,6-tetrahydropyrimidin-2-ylcarbamoyl)-butyl)-thiophen-2-yl)-propionic Acid

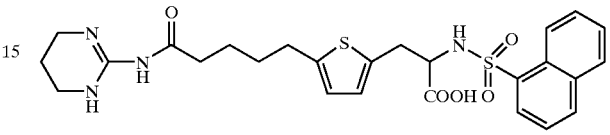

a) (2S)-2-Amino-3-(5-bromo-thiophen-2-yl)-propionic Acid 17.1 g (0.1 mol) of (S)-thienylalanine were suspended in 250 ml of AcOH and 5 ml (0.1 mol) of bromine were slowly added. The thienylalanine dissolved and a new precipitate formed. The mixture was stirred for 15 h, the product was filtered and washed with AcOH. Yield: 24 g.

MS (FAB): m/e=251.9, 249.9 (M+H$^+$, 100%).

b) (2S)-2-Benzyloxycarbonylamino-3-(5-bromo-thiophen-2-yl)-propionic Acid

To 24 g (0.096 mol) of the compound of step a) in 500 ml of DMF 24 g (0.096 mol) of N-benzyloxycarbonyloxysuccinimide were added at 0° C. The mixture was brought to pH 7 with N,N-diisopropylethylamine, slowly warmed to room temperature and stirred at room temperature for 12 h. The solvent was removed in vacuo. The residue was dissolved in EE and extracted with water, dried over MgSO$_4$ and filtered. The solvent was removed in vacuo. The crude product was purified by flash chromatography on silica gel (DCM/MeOH/AcOH/H$_2$O 95/5/0.5/0.5). Yield: 25 g.

MS (ES$^+$): m/e=386.1, 384.1 (M+H$^+$, 50%), 342.1, 340.1 (100%).

c) (2S)-2-Benzyloxycarbonylamino-3-(5-bromo-thiophen-2-yl)-propionic Acid tert-butyl ester To 20.0 g (52.1 mmol) of the compound of step b) in 50 ml of chloroform were added under stirring at 0° C. 256.8 g (2.21 mol) of tert-butyl acetate and 15.4 g (157 mmol) of conc. H$_2$SO$_4$ and 2.75 g (24.1 mmol) of 20% oleum. The reaction mixture was slowly brought to room temperature and stirred for 20 h. After cooling to 0° C. 10% KHCO$_3$ solution was added until pH 7 was reached. The mixture was extracted three times with DCM and the combined organic phases were washed with brine, dried over MgSO$_4$, filtered and the solvent removed in vacuo. The product was further purified by chromatography on silica gel (EE/n-heptane 1/9). Yield: 18.1 g.

MS (ES$^+$): m/e=442.1, 440.1 (M+H$^+$, 70%), 386.0, 384.0 (100%).

d) Pent-4-enoic acid benzyl ester

To 10.53 g (105 mmol) of pent-4-enoic acid in 150 ml ethanol was added 17.1 g (52.5 mmol) of Cs$_2$CO$_3$ and the reaction mixture was stirred at 40° C. for 2 h. The solvent was removed in vacuo, the residue coevaporated three times with toluene and then dissolved in 150 ml of DMF. 17.96 g (105 mmol) of benzyl bromide were added and the reaction mixture stirred at room temperature for 48 h. The reaction mixture was filtered, diluted with water and extracted three times with heptane. The combined organic phases were dried over MgSO$_4$, filtered and the solvent was removed in vacuo. Yield: 19.92 g.

MS (ES+): m/e=191.0 (M+H+, 100%), 173.1 (50%), 91.0 (80%).

e) 5-(5-((2S)-2-Benzyloxycarbonylamino-2-tert-butoxycarbonyl-ethyl)-thiophen-2-yl)-pent-4-enoic acid benzyl ester A mixture of 10.80 g (56.77 mmol) of the compound of step d), 5.0 g of the compound of step c), 0.88 g (3.18 mmol) of tetrabutylammonium chloride, 3.92 g (28.4 mmol) of $K_2CO_3$ and 128 mg of palladium acetate in 3 ml of absolute DMF was heated to 100° C. for 3 h. The solvent was removed in vacuo and the crude product was purified by flash chromatography on silica gel (EE/n-heptane 1/4 to 1/1). Yield: 3.1 g.

MS (ES+): m/e=550.2 (M+H+, 100%), 494.2 (60%), 450.2 (20%), 90.9 (60%).

f) 5-(5-((2S)-2-Amino-2-tert-butoxycarbonyl-ethyl)-thiophen-2-yl)-pentanoic acid 1.5 g (2.73 mmol) of the compound of step e) were dissolved in 20 ml of AcOH and hydrogenated over 5% Pd/C at room temperature and under a hydrogen pressure of about 1 bar for 4 h. The reaction mixture was filtered, the solvent was removed in vacuo and the crude product was purified by flash chromatography on silica gel (DCM/MeOH/$H_2O$/AcOH 90/10/1/1). Three products were obtained:

Compound 1f)-1: 5-(5-((2S)-2-Benzyloxycarbonylamino-2-tert-butoxycarbonyl-ethyl)-thiophen-2-yl)-pentanoic acid. Yield: 215 mg.

MS (ES+): m/e=462.1 (M+H+, 100%), 406.1 (50%), 328.1 (25%).

Compound 1f)-2: 5-(5-((2S)-2-Amino-2-tert-butoxycarbonyl-ethyl)-thiophen-2-yl)-pentanoic acid benzyl ester. Yield: 101 mg.

MS (ES+): m/e=418.2 (M+H+, 100%).

Compound 1f)-3: 5-(5-((2S)-2-Amino-2-tert-butoxycarbonyl-ethyl)-thiophen-2-yl)-pentanoic acid. Yield: 471 mg.

MS (ES+): m/e 328.1 (M+H+, 100%), 272.0 (20%).

g) 5-(5-((2S)-2-tert-Butoxycarbonyl-2-(naphthalene-1-sulfonylamino)-ethyl)-thiophen-2-yl)-pentanoic Acid To 100 mg (0.3 mmol) of the compound 1f)-3 of step f) in 3 ml of absolute DMF were added at 0° C. 0.61 mmol of naphthalene-1-sulfonyl chloride and 0.92 mmol of N,N-diisopropylethylamine, and the reaction mixture was stirred at 0° C. for 3 h. The solvent was removed in vacuo, the residue was dissolved in EE and extracted twice with aqueous $KHSO_4$ solution and once with brine. The organic phase was dried over $MgSO_4$, filtered and the solvent was removed in vacuo. Yield: 105 mg.

MS (ES+): m/e=518.2 (M+H+, 50%), 462.1 (100%).

h) (2S)-2-(Naphthalene-1-sulfonylamino)-3-(5-(4-(1,4,5,6-tetrahydropyrimidin-2-ylcarbamoyl)-butyl)-thiophen-2-yl)-propionic acid tert-butyl ester To 39 mg of the compound of step g) in 3 ml of absolute THF were added 9.0 mg of 1,4,5,6-tetrahydropyrimidin-2-ylamine, 39 mg of N,N-diisopropylethylamine and 31.5 mg of O-(7-azabenzotriazol-1-yl)-1,1,3,3-tetramethyluronium hexafluorophosphate (HATU), and the reaction mixture was stirred for 3 h at room temperature. The solvent was removed in vacuo, the residue was dissolved in EE and extracted twice with aqueous $NaHCO_3$ solution and once with brine. The organic phase was dried over $MgSO_4$, filtered and the solvent was removed in vacuo, the crude product was purified by flash chromatography on silica gel (DCM/MeOH/$H_2O$/AcOH 97.5/2.5/0.25/0.25). Yield: 32 mg.

MS (ES+): m/e=599.2 (M+H+, 100%), 573.2 (30%).

i) (2S)-2-(Naphthalene-1-sulfonylamino)-3-(5-(4-(1,4,5,6-tetrahydropyrimidin-2-ylcarbamoyl)-butyl)-thiophen-2-yl)-propionic acid 32 mg of the compound of step h) were dissolved in 3.4 ml of cooled 95% TFA and stirred for 2 h at 0° C. and then for 2 h at room temperature. The TFA was removed in vacuo, the product was coevaporated with toluene and lyophilized. Yield: 32 mg (TFA salt).

MS (ES+): m/e=543.1 (M+H+, 100%); 517.2 (25%).

Example 2

(2S)-2-(Naphthalene-2-sulfonylamino)-3-(5-(4-(1,4,5,6-tetrahydropyrimidin-2-ylcarbamoyl)-butyl)-thiophen-2-yl)-propionic acid

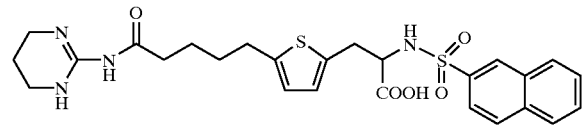

a) 5-(5-((2S)-2-tert-Butoxycarbonyl-2-(naphthalene-2-sulfonylamino)-ethyl)-thiophen-2-yl)-pentanoic acid The compound was synthesized in analogy to example 1g) from the compound 1f)-3 of example 1, step f) and naphthalene-2-sulfonyl chloride. Yield: 34.2%.

MS (ES+): m/e=518.2 (M+H+, 35%), 462.1 (100%).

b) (2S)-2-(Naphthalene-2-sulfonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 100%.

MS (ES+): m/e=599.2 (M+H+, 100%), 573.2 (30%), 254.2 (10%), 226.1 (20%).

c) (2S)-2-(Naphthalene-2-sulfonylamino)-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 99%.

MS (ES+): m/e=543.1 (M+H+, 100%); 517.2 (25%), 226.1 (15%), 130.0 (20%).

Example 3

(2S)-2-Benzenesulfonylamino-3-(5-(4-(1,4,5,6-tetrahydropyrimidin-2-ylcarbamoyl)-butyl)-thiophen-2-yl)-propionic acid

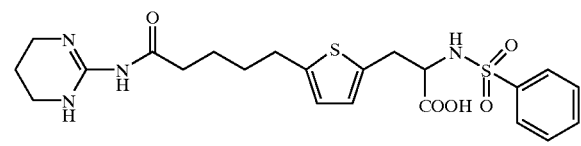

a) 5-(5-((2S)-2-benzenesulfonylamino-2-tert-butoxycarbonyl-ethyl)-thiophen-2-yl)-pentanoic acid The compound was synthesized in analogy to example 1g) from the compound 1f)-3 of example 1, step f) and benzenesulfonyl chloride. Yield: 41.4%.

MS (ES+): m/e=468.2 (M+H+, 25%), 412.1 (100%), 394.1 (40%).

b) (2S)-2-Benzenesulfonylamino-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 82%.

MS (ES+): m/e=549.2 (M+H+, 100%), 523.2 (15%).

c) (2S)-2-Benzenesulfonylamino-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 87%.

MS (ES+): m/e=493.1 (M+H+, 100%); 467.2 (25%), 198.0 (15%).

Example 4

(2S)-2-(4-Chlorobenzenesulfonylamino)-3-(5-(4-(1,4,5,6-tetrahydropyrimidin-2-ylcarbamoyl)-butyl)-thiophen-2-yl)-propionic acid

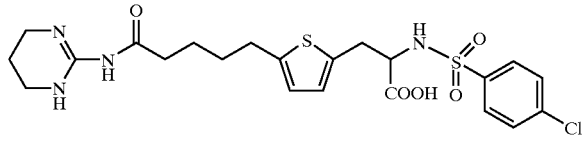

a) 5-(5-((2S)-2-tert-Butoxycarbonyl-2-(4-Chlorobenzenesulfonylamino)-ethyl)-thiophen-2-yl)-pentanoic acid The compound was synthesized in analogy to example 1g) from the compound 1f)-3 of example 1, step f) and 4-Chlorobenzenesulfonyl chloride. Yield: 47.7%.

MS (ES$^+$): m/e=504.2, 502.1 (M+H$^+$, 10%, 20%), 448.1, 446.1 (40%, 100%).

b) (2S)-2-(4-Chlorobenezenesulfonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 53%.

MS (ES$^+$): m/e=585.1, 583.1 (M+H$^+$, 45%, 100%).

c) (2S)-2-(4-Chlorobenzenesulfonylamino)-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 80%.

MS (ES$^+$): m/e=529.1, 527.1 (M+H$^+$, 45%, 100%).

Example 5

(2S)-2-(3-Chlorobenzenesulfonylamino)-3-(5-(4-(1,4,5,6-tetrahydropyrimidin-2-ylcarbamoyl)-butyl)-thiophen-2-yl)-propionic acid

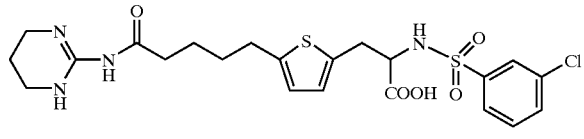

a) 5-(5-((2S)-2-tert-Butoxycarbonyl-2-(3-chlorobenezenesulfonylamino)-ethyl)-thiophen-2-yl)-pentanoic acid The compound was synthesized in analogy to example 1g) from the compound 1f)-3 of example 1, step f) and 3-chlorobenzenesulfonyl chloride. Yield: 37.9%.

MS (ES$^+$): m/e=504.2, 502.1 (M+H$^+$, 10%, 20%), 448.1, 446.1 (40%,100%), 430.1, 428.1 (15%, 30%).

b) (2S)-2-(3-Chlorobenzenesulfonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 53%.

MS (ES$^+$): m/e=585.1, 583.1 (M+H$^+$, 45%,100%), 559.2, 557.2 (10%, 20%).

c) (2S)-2-(3-Chlorobenzenesulfonylamino)-3-(5-(4-(1,4,5,6-tetrahydropyrimidin-2-ylcarbamoyl)-butyl)-thiophen-2-yl)propionic acid The compound was synthesized in analogy to example 1l) from the compound of step b). Yield: 79%.

MS (ES$^+$): m/e=529.1, 527.1 (M+H$^+$, 45%, 100%).

Example 6

(2S)-3-(5-(4-(1,4,5,6-Tetrahydropyrimidin-2-ylcarbamoyl)-butyl)-thiophen-2-yl)-2-(4-trifluoromethylbenzenesulfonylamino)-propionic acid

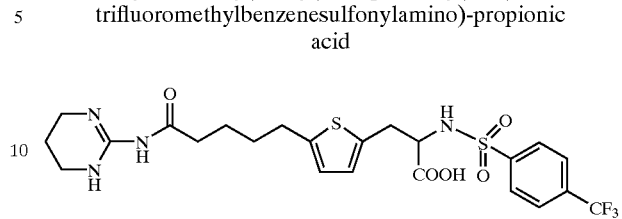

a) 5-(5-((2S)-2-tert-Butoxycarbonyl-2-(4-trifluoromethylbenzenesulfonylamino)-ethyl)-thiophen-2-yl)-pentanoic acid The compound was synthesized in analogy to example 1g) from the compound 1f)-3 of example 1, step f) and 4-trifluoromethylbenzenesulfonyl chloride. Yield: 92%.

MS (ES$^-$): m/e=534.4 (M–H$^+$, 10%), 112.9 (100).

b) (2S)-3-(5-(4-(1,4,5,6-Tetrahydropyrimidin-2-ylcarbamoyl)-butyl)-thiophen-2-yl)-2-(4-trifluoromethylbenzenesulfonylamino)-propionic acid tert-butyl ester The compound was synthesized in analogy to example 1h) from the compound of step a). Yield: 93%.

MS (ES$^+$): m/e=617.4 (M+H$^+$, 100%).

c) (2S)-3-(5-(4-(1,4,5,6-Tetrahydropyrimidin-2-ylcarbamoyl)-butyl)-thiophen-2-yl)-2-(4-trifluoromethylbenzenesulfonylamino)-propionic acid The compound was synthesized in analogy to example 1i) from the compound of step b). Yield: 79%.

MS (ES$^+$): m/e=561.4 (M+H$^+$, 100%).

Example 7

(2S)-3-(5-(4-(1,4,5,6-Tetrahydropyrimidin-2-ylcarbamoyl)-butyl)-thiophen-2-yl)-2-(2,2,2-trifluoroethanesulfonylamino)-propionic acid

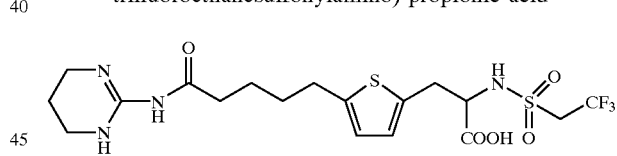

a) 5-(5-((2S)-2-tert-Butoxycarbonyl-2-(2,2,2-trifluoroethanesulfonylamino)-ethyl)-thiophen-2-yl)-pentanoic acid The compound was synthesized in analogy to example 1g) from the compound 1f)-3 of example 1, step f) and 2,2,2-trifluoroethanesulfonyl chloride. Yield: 42%.

MS (ES$^+$): m/e=474.0 (M+H$^+$, 15%), 418.0 (100%).

b) (2S)-3-(5-(4-(1,4,5,6-Tetrahydropyrimidin-2-ylcarbamoyl)-butyl)-thiophen-2-yl)-2-(2,2,2-trifluoroethanesulfonylamino)-propionic acid tert-butyl ester The compound was synthesized in analogy to example 1h) from the compound of step a). Yield: 56%.

MS (ES$^+$): m/e=555.2 (M+H$^+$, 100%).

c) (2S)-3-(5-(4-(1,4,5,6-Tetrahydropyrimidin-2-ylcarbamoyl)-butyl)-thiophen-2-yl)-2-(2,2,2-trifluoroethanesulfonylamino)-propionic acid The compound was synthesized in analogy to example 1i) from the compound of step b). Yield: 82%.

MS (ES$^+$): m/e=499.1 (M+H$^+$, 100%).

Example 8

(2S)-2-(Propane-1-sulfonylamino)-3-(5-(4-(1,4,5,6-tetrahydropyrimidin-2-ylcarbamoyl)-butyl)-thiophen-2-yl)-propionic acid

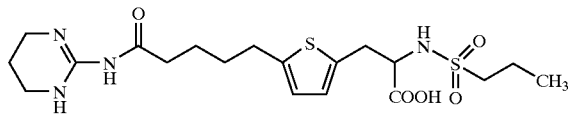

a) 5-(5-((2S)-2-tert-Butoxycarbonyl-2-(propane-1-sulfonylamino)-ethyl)-thiophen-2-yl)-pentanoic acid The compound was synthesized in analogy to example 1g) from the compound 1f)-3 of example 1, step f) and propane-1-sulfonyl chloride. Yield: 50%.
MS (ES$^+$): m/e=434.1 (M+H$^+$, 15%), 378.1 (100%).

b) (2S)-2-(Propane-1-sulfonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 52%.
MS (ES$^+$): m/e=515.3 (M+H$^+$, 100%).

c) (2S)-2-(Propane-1-sulfonylamino)-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 91%.
MS (ES$^+$): m/e=459.2 (M+H$^+$, 100%).

Example 9

(2S)-2-(Butane-1-sulfonylamino)-3-(5-(4-(1,4,5,6-tetrahydropyrimidin-2-ylcarbamoyl)-butyl)-thiopen-2-yl)-propionic acid

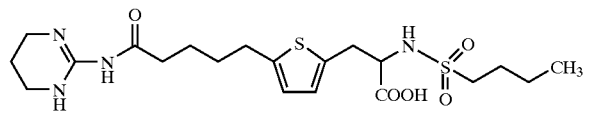

a) 5-(5-((2S)-2-tert-Butoxycarbonyl-2-(butane-1-sulfonylamino)-ethyl)-thiophen-2-yl)-pentanoic acid The compound was synthesized in analogy to example 1g) from the compound 1f)-3 of example 1, step f) and butane-1-sulfonyl chloride. Yield: 47%.
MS (ES$^+$): m/e=448.1 (M+H$^+$, 10%), 392.1 (60%), 248.1 (100%).

b) (2S)-2-(Butane-1-sulfonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 42%.
MS (ES$^+$): m/e=529.3 (M+H$^+$, 100%).

c) (2S)-2-(Butane-1-sulfonylamino)-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 100%.
MS (ES$^+$): m/e=473.2 (M+H$^+$, 80%).

Example 10

(2S)-2-(4-tert-Butylbenzenesulfonylamino)-3-(5-(4-(1,4,5,6-tetrahydropyrimidin-2-ylcarbamoyl)-butyl)-thiophen-2-yl)-propionic acid

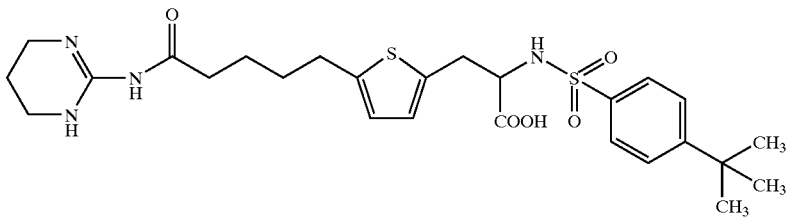

a) 5-(5-((2S)-2-tert-Butoxycarbonyl-2-(4-tert-butylbenzenesulfonylamino)-ethyl)-thiophen-2-yl)-pentanoic acid The compound was synthesized in analogy to example 1g) from the compound 1f)-3 of example 1, step f) and 4-tert-butylbenzenesulfonyl chloride. Yield: 44%.
MS (ES$^+$): m/e=524.1 (M+H$^+$, 40%,), 468.1 (80%), 242.0 (100%).

b) (2S)-2-(4-tert-Butylbenzenesulfonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 58%.
MS (ES$^+$): m/e=605.3 (M+H$^+$, 100%).

c) (2S)-2-(4-tert-Butylbenzenesulfonylamino)-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 95%.
MS (ES+): m/e=549.2 (M+H+, 100%).

Example 11

(2S)-2-Benzyloxycarbonylamino-3-(5-(4-(1,4,5,6-tetrahydropyrimidin-2-ylcarbamoyl)-butyl)-thiophen-2-yl)-propionic acid

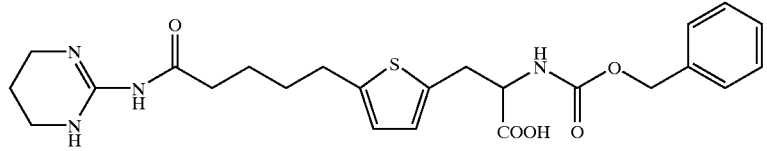

a) (2S)-2-Benzyloxycarbonylamino-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound 1f)-1 of example 1, step f). Yield: 63%.

MS (FAB): m/e=543.3 (M+H+, 100%), 487.2 (20%), 184.2 (60%).

b) (2S)-2-Benzyloxycarbonylamino-3-(5-(4-(1,4,5,6-tetrahydropyrimidin-2-ylcarbamoyl)-butyl)-thiophen-2-yl)-propionic acid The compound was synthesized in analogy to example 1i) from the compound of step a). Yield: 45%.
MS (ES+): m/e=487.0 (M+H+, 100%).

Example 12

(2S)-2-(Adamantan-1-ylmethoxycarbonylamino)-3-(5-(4-(1,4,5,6-tetrahydropyrimidin-2-ylcarbamoyl)-butyl)-thiophen-2-yl)-propionic acid

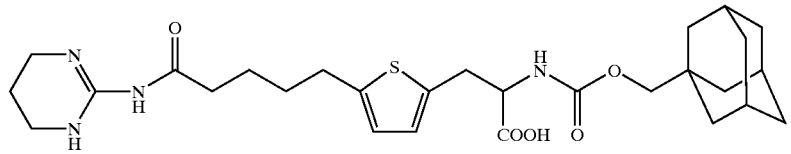

a) 5-(5-((2S)-2-(Adamantan-1-ylmethoxycarbonylamino)-2-tert-butoxycarbonyl-ethyl)-thiophen-2-yl)-pentanoic acid To 100 mg (0.258 mmol) of the compound 1f)-3 of example 1f) in 3 ml of dioxane were added 3 ml of saturated aqueous NaHCO₃ solution and 80 mg (0.258 mmol) of N-(adamantan-1-ylmethoxycarbonyloxy)succinimide, and the reaction mixture was stirred for 3 h at room temperature. The solvent was removed in vacuo and the residue dissolved in EE, the solution extracted with water, dried over MgSO₄, filtered, and the solvent removed in vacuo. Yield: 63 mg.

MS (ES+): m/e=520.3 (M+H+, 50%).

b) (2S)-2-(Adamantan-1-ylmethoxycarbonylamino)-3-(5-(4-(1,4,5,6-tetrahydropyrimidin-2-ylcarbamoyl)-butyl)-thiophen-2-yl)-propionic acid tert-butyl ester The compound was synthesized in analogy to example 1h) from the compound of step a). Yield: 41%.

MS (FAB): m/e=601.3 (M+H+, 100%), 545.3 (10%).

c) (2S)-2-(Adamantan-1-ylmethoxycarbonylamino)-3-(5-(4-(1,4,5,6-tetrahydropyrimidin-2-ylcarbamoyl)-butyl)-thiophen-2-yl)-propionic acid The compound was synthesized in analogy to example 1i) from the compound of step b). Yield: 33%.
MS (ES+): m/e=545.3 (M+H+, 100%).

Example 13

(2S)-2-Benzyloxycarbonylamino-3-(5-(5-(1,4,5,6-tetrahydropyrimidin-2-ylcarbamoyl)-pentyl)-thiophen-2-yl)-propionic acid

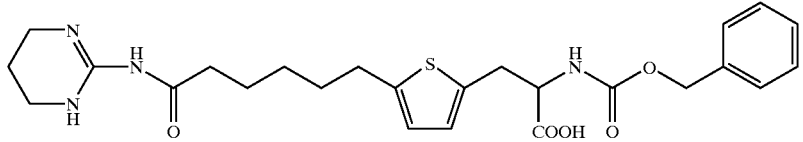

a) Hex-5-enoic acid benzyl ester

The compound was synthesized in analogy to example 1d) starting from hex-5-enoic acid. Yield: 100%.
MS (CI+): m/e=205.1 (M+H+, 25%), 187.1 (100%), 169.0 (10%), 91.0 (65%).

b) 6-(5-((2S)-2-Benzyloxycarbonylamino-2-tert-butoxycarbonyl-ethyl)-thiophen-2-yl)-hex-5-enoic acid benzyl ester The compound was synthesized in analogy to example 1e) from the compound of step a) and the compound of example 1c). Yield: 32%.

MS (FAB): m/e=564.2 (M+H+, 90%), 508.1 (80%), 464.2 (50%), 412.1 (65%), 299.0 (100%).

c) 6-(5-((2S)-2-Benzyloxycarbonylamino-2-tert-butoxycarbonyl-ethyl)-thiophen-2-yl)-hexanoic acid 1.5 g of the compound of step b) were dissolved in 20 ml of AcOH and hydrogenated over 5% Pd/C at room temperature under a hydrogen pressure of about 1 bar for 4 h. The reaction mixture was filtered, the solvent was removed in vacuo and the crude product was purified by flash chromatography on silica gel (DCM/MeOH/H$_2$O/AcOH 90/10/1/1). Three products were obtained:

Compound 13c)-1: 6-(5-((2S)-2-Benzyloxycarbonylamino-2-tert-butoxycarbonyl-ethyl)-thiophen-2-yl)-hexanoic acid. Yield: 193 mg.

MS (ES$^+$): m/e=476.2 (M+H$^+$, 100%), 432.2 (25%), 420.2 (50%).

Compound 13c)-2: 6-(5-((2S)-2-Amino-2-tert-butoxycarbonyl-ethyl)-thiophen-2-yl)-hexanoic acid benzyl ester. Yield: 55 mg.
MS (ES$^+$): m/e=432.2 (M+H$^+$, 100%).
Compound 13c)-3: 6-(5-((2S)-Amino-2-tert-butoxycarbonyl-ethyl)-thiophen-2-yl)-hexanoic acid. Yield: 280 mg.
MS (ES$^+$): m/e=342.2 (M+H$^+$, 100%), 286.1 (20%).

d) (2S)-2-Benzyloxycarbonylamino-3-(5-(5-(1,4,5,6-tetrahydropyrimidin-2-ylcarbamoyl)-pentyl)-thiophen-2-yl)-propionic acid tert-butyl ester The compound was synthesized in analogy to example 1h) from the compound 13c)-1 of step c). Yield: 41%.
MS (FAB): m/e=557.2 (M+H$^+$, 100%), 501.2 (20%).

e) (2S)-2-Benzyloxycarbonylamino-3-(5-(5-(1,4,5,6-tetrahydropyrimidin-2-ylcarbamoyl)-pentyl)-thiophen-2-yl)-propionic acid The compound was synthesized in analogy to example 1i) from the compound of step d). Yield: 44%.
MS (ES$^+$): m/e=500.9 (M+H$^+$, 100%), 410.9 (5%).

Example 14
(2S)-2-Benzyloxycarbonylamino-3-(5-(5-(1,4,5,6-tetrahydropyrimidin-2-ylcarbamoyl)-pent-1-enyl)-thiophen-2-yl)-propionic acid

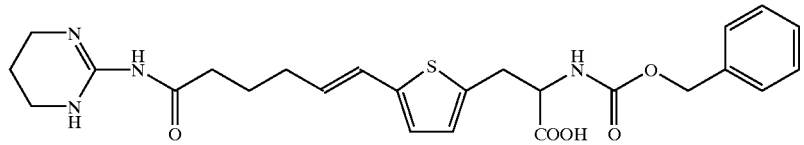

a) (2S)-2-Benzyloxycarbonylamino-3-(5-(5-(1,4,5,6-tetrahydropyrimidin-2-ylcarbamoyl)-pent-1-enyl)-thiophen-2-yl)-propionic acid tert-butyl ester To 224 mg of the compound of example 13b) in 5 ml of absolute DMF were added 197 mg of 1,4,5,6-tetrahydropyrimidin-2-ylamine, and the reaction mixture was stirred at room temperature for 14 h. The solvent was removed in vacuo and the crude product was purified by flash chromatography on silica gel (DCM/MeOH/H$_2$O/AcOH 90/5/0.5/0.5). Yield: 171 mg.

MS (ES$^+$): m/e=555.3 (M+H$^+$, 100%); 354.2 (5%).

b) (2S)-2-Benzyloxycarbonylamino-3-(5-(5-(1,4,5,6-tetrahydropyrimidin-2-ylcarbamoyl)-pent-1-enyl)-thiophen-2-yl)-propionic acid The compound was synthesized in analogy to example 1i) from the compound of step a). Yield: 15%.

MS (ES$^+$): m/e=499.5 (M+H$^+$, 70%).

Example 15

(2S)-2-Benzyloxycarbonylamino-3-(5-(4-(1,4,5,6-tetrahydropyrimidin-2-ylcarbamoyl)-but-1-enyl)-thiophen-2-yl)-propionic acid

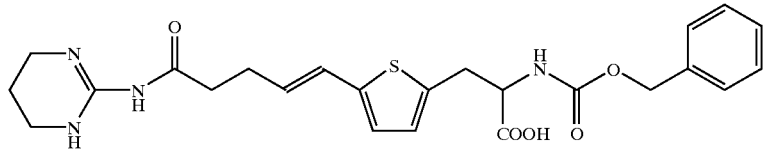

a) (2S)-2-Benzyloxycarbonylamino-3-(5-(4-(1,4,5,6-tetrahydropyrimidin-2-ylcarbamoyl)-but-1-enyl)-thiophen-2-yl)-propionic acid tert-butyl ester The compound was synthesized in analogy to example 14a) from the compound of example 1e). Yield: 100%.
MS (FAB): m/e=541.3 (M+H$^+$, 100%); 485.2 (20%), 276.1 (20%).

b) (2S)-Benzyloxycarbonylamino-3-(5-(4-(1,4,5,6-tetrahydropyrimidin-2-ylcarbamoyl)-but-1-enyl)-thiophen-2-yl)-propionic acid The compound was synthesized in analogy to example 1i) from the compound of step a). Yield: 6%.
MS (ES$^+$): m/e=485.5 (M+H$^+$, 70%); 204.0 (40%),147.9 (100%).

Pharmacological Testing
1) Kistrin Binding Assay

The inhibition of the binding of kistrin to human vitronectin receptor (VnR) described below is a test method by which the antagonistic action of the compounds of the invention on the vitronectin receptor $\alpha_v\beta_3$ can be determined ($\alpha_v\beta_3$ ELISA Test; the test method is abbreviated as "K/VnR" in the listing of the test results).

Purification of Kistrin

Kistrin was purified according to the methods of Dennis et al., as described in Proc. Natl. Acad. Sci. USA 87 (1989) 2471 and Proteins: Structure, Function and Genetics 15(1993)312.

Purification of Human Vitronectin Receptor ($\alpha_v\beta_3$)

Human vitronectin receptor was obtained from the human placenta according to the method of Pytela et al., Methods Enzymol. 144 (1987) 475. Human vitronectin receptor $\alpha_v\beta_3$ can also be obtained from some cell lines (for example from 293 cells, a human embryonic kidney cell line) which are cotransfected with DNA sequences for both subunits $\alpha_v$ and $\beta_3$ of the vitronectin receptor. The subunits were extracted with octyl glycoside and then chromatographed through concanavalin A, heparin-Sepharose and S-300.

Monoclonal Antibodies

Murine monoclonal antibodies which are specific for the $\beta_3$ subunits of the vitronectin receptor, were prepared according to the method of Newman et al., Blood (1985) 227, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates were coated with a solution of kistrin (0.002 mg/ml) according to the method of Dennis et al., as described in Proteins: Structure, Function and Genetics 15 (1993) 312. The plates were then washed twice with PBS/0.05% Tween-20 and blocked by incubating (60 min) with bovine serum albumin (BSA, 0.5%, RIA grade or better) in buffer solution (Tris-HCl (50 mM), NaCl (100 mM), $MgCl_2$ (1 mM), $CaCl_2$ (1 mM), $MnCl_2$ (1 mM), pH 7). Solutions of known inhibitors and of the test substances were prepared in concentrations from $2 \times 10^{-12}$ to $2 \times 10^{-6}$ mol/l in assay buffer (BSA (0.5%, RIA grade or better); Tris-HCl (50 mM), NaCl (100 mM), $MgCl_2$ (1 mM), $CaCl_2$ (1 mM), $MnCl_2$ (1 mM), pH 7). The blocked plates were emptied, and in each case 0.025 ml of this solution which contained a defined concentration ($2 \times 10^{-12}$ to $2 \times 10^{-6}$ mol/l) either of a known inhibitor or of a test substance, were added to each well. 0.025 ml of a solution of the vitronectin receptor in assay buffer (0.03 mg/ml) is pipetted into each well of the plate and the plate was incubated at room temperature for 60–180 min on a shaker. In the meantime, a solution (6 ml/plate) of a murine monoclonal antibody specific for the $\beta_3$ subunit of the vitronectin receptor was prepared in assay buffer (0.0015 mg/ml). A second rabbit antibody (0.001 ml of stock solution/6 ml of the murine monoclonal anti-$\beta_3$ antibody solution) which is an anti-mouse Fc HRP antibody conjugate was added to this solution, and this mixture of murine anti-$\beta_3$ antibody and rabbit anti-mouse Fc HRP antibody conjugate was incubated during the time of the receptor-inhibitor incubation. The test plates were washed four times with PBS solution which contains 0.05% Tween-20, and in each case 0.05 ml/well of the antibody mixture was pipetted into each well of the plate and incubated for 60–180 min. The plate was washed four times with PBS/0.05% Tween-20 and then developed with 0.05 ml/well of a PBS solution which contained 0.67 mg/ml of o-phenylenediamine and 0.012% of $H_2O_2$. Alternatively to this, o-phenylenediamine can be employed in a buffer (pH 5) which contains $Na_3PO_4$ and citric acid. The color development was stopped using 1 N $H_2SO_4$ (0.05 ml/well). The absorption for each well was measured at 492–405 nm and the data were evaluated by standard methods.

2) Vitronectin/293 Cell Test

In this test the inhibition of binding of 293 cells to human vitronectin (Vn) by the compounds of the invention is determined (the test method is abbreviated as "Vn/293 cell test" in the listing of the test results).

Purification of Human Vitronectin

Human vitronectin was isolated from human plasma and purified by affinity chromatography according to the method of Yatohgo et al., Cell Structure and Function 23 (1988) 281.

Cell Test 293 cells, a human embryonic kidney cell line, which were cotransfected with DNA sequences for the $\alpha_v$ and $\beta_3$ subunits of the vitronectin receptor $\alpha_v\beta_3$, were selected for a high rate of expression (>500,000 $\alpha_v\beta_3$ receptors/cell) according to the FACS method. The selected cells were cultured and sorted again by means of FACS in order to obtain a stable cell line (15 D) with expression rates >1,000,000 copies of $\alpha_v\beta_3$ per cell.

A Linbro 96-well tissue culture plate with a flat bottom was coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2 \times 10^{-3}$ mol/l in glucose-containing DMEM medium were prepared and 0.05 ml/well of the solution were added to the plate in each case. The cells which expressed high levels of $\alpha_v\beta_3$ (for example 15 D) were suspended in glucose-containing DMEM medium and the suspension was adjusted to a content of 25,000 cells/0.05 ml of medium. 0.05 ml of this cell suspension was added to each well and the plate was incubated at 37° C. for 90 min. The plate was washed 3 times with warm PBS in order to remove unbound cells. The bound cells were lyzed in citrate buffer (25 mM, pH 5.0) which contained 0.25% Triton X-100. The hexoseamidase substrate p-nitrophenyl-N-acetyl-β-D-glucosaminide was then added and the plate was incubated at 37° C. for 90 min. The reaction was stopped with a glycine (50 mM)/EDTA (5 mM) buffer (pH 10.4) and the absorption of each well was measured at 405 to 650 nm. The data were analyzed according to standard methods.

The following test results (inhibitory concentrations $IC_{50}$) were obtained.

| Compound | K/VnR $IC_{50}$ (μM) | Vn/293 cell test $IC_{50}$ (μM) |
|---|---|---|
| Example 1 | 0.023 | 0.42 |
| Example 2 | 0.015 | 0.33 |
| Example 3 | 0.0095 | 1.0 |
| Example 4 | 0.012 | 0.85 |
| Example 5 | 0.015 | 0.42 |
| Example 6 | 0.028 | 2.0 |
| Example 7 | 0.011 | 0.40 |
| Example 8 | 0.060 | 1.0 |
| Example 9 | 0.046 | 1.8 |
| Example 10 | 0.095 | 6.9 |
| Example 11 | 0.009 | 0.11 |
| Example 12 | 0.023 | 0.22 |
| Example 13 | 0.097 | 0.21 |
| Example 14 | 0.040 | 0.69 |
| Example 15 | 0.035 | 0.58 |

What is claimed is:
1. A compound of the formula I

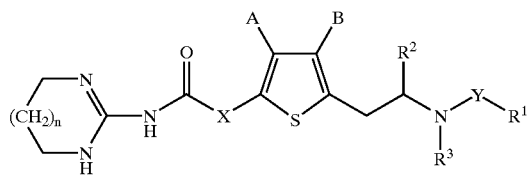

wherein

A and B which are individually selected from the group consisting of hydrogen, ($C_1$–$C_{18}$)-alkyl, ($C_3$–$C_4$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, fluorine, chlorine, bromine, cyano, trifluoromethyl, nitro, hydroxycarbonyl-, ($C_1$–$C_6$)-alkoxy, ($C_1$–$C_6$)-alkoxy-($C_1$–$C_6$)-alkyl, ($C_1$–$C_6$)-alkoxycarbonyl-, ($C_1$–$C_6$)-alkylcarbonyl-, ($C_5$–$C_{14}$)-arylcarbonyl-, ($C_1$–$C_6$)-alkylaminocarbonyl-, ($C_1$–$C_6$)-alkoxy-($C_1$–$C_6$)-alkoxy-($C_1$–$C_6$)-alkoxy, ($C_5$–$C_{14}$)-aryl-($C_1$–$C_8$)-alkylcarbonyl-, ($C_1$–$C_6$)-alkanoylamino-, ($C_1$–$C_6$)-alkylamino-, di-(($C_1$–$C_6$)-alkyl)amino-, ($C_1$–$C_6$)-alkylsulfonyl- and aminosulfonyl-, or A and B bonded to the thiophene ring together with the carbon atoms to which they are bonded form an aromatic or non-aromatic ring system that is fused to the thiophene ring;

X is selected from the group consisting of ($C_3$–$C_6$)-alkanediyl, ($C_3$–$C_6$)-alkenediyl and ($C_3$–$C_6$)-alkynediyl, where in all these one carbon atom can be replaced by a heteroatom selected from the group consisting of nitrogen, oxygen and sulfur and where all these can be substituted by one or two of hydroxy and/or A;

Y is selected from the group consisting of a direct bond, —S(O)$_2$—, —C(O)—, —C(O)—O—, —S(O)$_2$—N(R$^{3'}$)— and —C(O)—N(R$^3$)—, the divalent residues of Y are bonded to R$^1$ via the free bond on their right side;

R$^1$ is selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl, (C$_5$–C$_{14}$)-aryl and (C$_5$–C$_{14}$)-aryl-(C$_1$–C$_8$)-alkyl, where the alkyl, cycloalkyl and aryl are unsubstituted or substituted with one to three members of the groups consisting of fluorine, chlorine, bromine, cyano, trifluoromethyl, nitro, hydroxycarbonyl-, (C$_1$–C$_6$)-alkyl, (C$_5$–C$_{14}$)-aryl, (C$_5$–C$_{14}$)-aryl-(C$_1$–C$_8$)-alkyl-, (C$_1$–C$_6$)-alkoxy, (C$_1$–C$_6$)-alkoxy-(C$_1$–C$_6$)-alkyl-, (C$_1$–C$_6$)-alkoxycarbonyl-, (C$_1$–C$_6$)-alkylcarbonyl-, (C$_1$–C$_6$)-alkylaminocarbonyl-, (C$_1$–C$_6$)-alkoxy-(C$_1$–C$_6$)-alkoxy-, (C$_5$–C$_{14}$)-arylcarbonyl-, (C$_5$–C$_{14}$)-aryl-(C$_1$–C$_8$)-alkylcarbonyl-, (C$_1$–C$_6$)-alkanoylamino-, (C$_5$–C$_{14}$)-arylsulfonylamino-, (C$_1$–C$_6$)-alkylsulfonylamino-, (C$_1$–C$_6$)-alkylamino-, di-((C$_1$–C$_6$)-alkyl)amino-, (C$_1$–C$_6$)-alkylsulfonyl-, (C$_1$–C$_6$)-alkylaminosulfonyl-, (C$_5$–C$_{14}$)-arylaminosulfonyl-, (C$_5$–C$_{14}$)-aryl-(C$_1$–C$_8$)-alkylaminosulfonyl-, (C$_5$–C$_{14}$)-arylsulfonyl-, (C$_5$–C$_{14}$)-aryl-(C$_1$–C$_8$)-alkylsulfonyl- and a residue of a saturated or partially unsaturated, monocyclic or polycyclic 3-membered to 14 membered ring which can contain one to four ring heteroatoms from the group consisting of nitrogen, oxygen and sulfur and unsubstituted or substituted with one or two members of the group consisting of A, =O and =S;

R$^2$ is selected from the group consisting of —C(O)R$^4$, —C(S)R$^4$, —S(O)$_2$R$^4$, —P(O)R$^4$R$^{4'}$ and a residue of a saturated or unsaturated 4-membered to 8-membered heterocycle which contains one to four heteroatoms from the group consisting of nitrogen, oxygen and sulfur;

R$^3$ and R$^{3'}$ which are individually selected from the group consisting of hydrogen, (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_3$–C$_{14}$)-cycloalkyl-(C$_1$–C$_8$)-alkyl-, (C$_5$–C$_{14}$)-aryl and (C$_5$–C$_{14}$)-aryl-(C$_1$–C$_8$)-alkyl-;

R$^4$ and R$^{4'}$ which are individually selected from the group consisting of hydroxy, (C$_1$–C$_8$)-alkoxy, (C$_5$–C$_{14}$)-aryl-(C$_1$–C$_8$)-alkoxy-, (C$_1$–C$_8$)-alkylcarbonyloxy-(C$_1$–C$_4$)-alkoxy-, (C$_5$–C$_{14}$)-aryl-(C$_1$–C$_8$)-alkylcarbonyloxy-(C$_1$–C$_8$)-alkoxy- and —NR$^5$R$^{5'}$;

R$^5$ and R$^{5'}$ which are individually selected from the group consisting of hydrogen, (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl and (C$_5$–C$_{14}$)-aryl-(C$_1$–C$_8$)-alkyl-, or R$^5$ and R$^{5'}$ together with the nitrogen atom to which they are bonded form a saturated or unsaturated 4-membered to 8-membered ring system which in addition to the nitrogen atom to which R$^5$ and R$^{5'}$ are bonded can contain one to three ring heteroatoms from the group consisting of nitrogen, oxygen and sulfur;

n is zero to two;

in all their steroisomeric forms and mixtures thereof in all ratios, and its pharmaceutically acceptable salts.

2. A compound of claim 1, wherein A and B bonded to the thiophene ring in the formula I are hydrogen;

X is selected from the group consisting of (C$_3$–C$_6$)-alkanediyl, (C$_3$–C$_6$)-alkenediyl and (C$_3$–C$_6$)-alkynediyl;

Y is —S(O)$_2$— or —C(O)—O;

R$^1$ is selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl, (C$_5$–C$_{14}$)-aryl and (C$_5$–C$_{14}$)-aryl-(C$_1$–C$_8$)-alkyl, where the alkyl, cycloalkyl and aryl are unsubstituted or substituted with one to three members of the groups consisting of fluorine, chlorine, bromine, cyano, trifluoromethyl, nitro, hydroxycarbonyl-, (C$_1$–C$_6$)-alkyl, (C$_5$–C$_{14}$)-aryl-(C$_1$–C$_8$)-alkyl, (C$_1$–C$_6$)-alkoxy, (C$_1$–C$_6$)-alkoxy-(C$_1$–C$_6$)-alkyl-, (C$_1$–C$_6$)-alkoxycarbonyl-, (C$_1$–C$_6$)-alkylcarbonyl-, (C$_1$–C$_6$)-alkylaminocarbonyl-, (C$_1$–C$_6$)-alkoxy-(C$_1$–C$_6$)-alkoxy-, (C$_5$–C$_{14}$)-arylcarbonyl-, (C$_5$–C$_{14}$)-aryl-(C$_1$–C$_8$)-alkylcarbonyl-, (C$_1$–C$_6$)-alkanoylamino-, (C$_5$–C$_{14}$)-arylsulfonylamino-, (C$_1$–C$_6$)-alkylsulfonylamino-, (C$_1$–C$_6$)-alkylamino-, di-((C$_1$–C$_6$)-alkyl)amino-, (C$_1$–C$_6$)-alkylsulfonyl-, (C$_1$–C$_6$)-alkylaminosulfonyl-, (C$_5$–C$_{14}$)-arylaminosulfonyl-, (C$_5$–C$_{14}$)-aryl-(C$_1$–C$_8$)-alkylaminosulfonyl-, (C$_5$–C$_{14}$)-arylsulfonyl-, (C$_5$–C$_{14}$)-aryl-(C$_1$–C$_8$)-alkylsulfonyl- and a residue of a saturated or partially unsaturated, monocyclic or polycyclic 3-membered to 14 membered ring which can contain one to four ring heteroatoms from the group consisting of nitrogen, oxygen and sulfur and unsubstituted or substituted with one or two members of the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl, (C$_5$–C$_{14}$)-aryl-(C$_1$–C$_8$)-alkyl-, fluorine, chlorine, bromine, cyano, trifluoromethyl, nitro, hydroxycarbonyl-, (C$_1$–C$_6$)-alkoxy, (C$_1$–C$_6$)-alkoxy-(C$_1$–C$_6$)-alkyl-, (C$_1$–C$_6$)-alkoxycarbonyl-, (C$_1$–C$_6$)-alkyl-carbonyl-, (C$_5$–C$_{14}$)-arylcarbonyl-, (C$_1$–C$_6$)-alkylaminocarbonyl-, (C$_1$–C$_6$)-alkoxy-(C$_1$–C$_6$)-alkoxy-, (C$_5$–C$_{14}$)-aryl-(C$_1$–C$_8$)-alkyolcarbonyl-, (C$_1$–C$_6$)-alkanoylamino-, (C$_1$–C$_6$)-alkylamino, di-((C$_1$–C$_6$)-alkyl)amino-, (C$_1$–C$_6$)-alkylsulfonyl-, aminosulfonyl-, =O and =S;

R$^2$ is —C(O)R$^4$;

R$^3$ is selected from the group consisting of hydrogen, (C$_1$–C$_6$)-alkyl and (C$_5$–C$_{14}$)-aryl-(C$_1$–C$_8$)-alkyl-;

R$^4$ is selected from the group consisting of hydroxy, (C$_1$–C$_8$)-alkoxy, (C$_1$–C$_8$)-alkylcarbonyloxy-(C$_1$–C$_4$)-alkoxy- and —NR$^5$R$^{5'}$;

R$^5$ and R$^{5'}$ which are individually selected from the group consisting of hydrogen, (C$_1$–C$_6$)-alkyl and (C$_5$–C$_{14}$)-aryl-(C$_1$–C$_8$)-alkyl-, or R$^5$ and R$^{5'}$ together with the nitrogen atom to which they are bonded form a 4- to 8-membered ring system which in addition to the nitrogen atom to which R$^5$ and R$^{5'}$ are bonded can contain one to three ring heteroatoms from the group consisting of nitrogen, oxygen and sulfur and which is unsaturated or saturated;

n is zero or one;

in all their stereoisomeric forms and mixtures thereof in all ratios, and its pharmaceutically acceptable salts.

3. A compound of claim 1, wherein A and B bonded to the thiophene ring in the formula I are hydrogen;

X is selected from the group consisting of (C$_3$–C$_6$)-alkanediyl, (C$_3$–C$_6$)-alkenediyl and (C$_3$–C$_6$)-alkynediyl;

Y is —S(O)$_2$— or —C(O)—O—;

R$^1$ is selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl and (C$_5$–C$_{14}$)-aryl-(C$_1$–C$_8$)-alkyl-, where the alkyl, cycloalkyl and aryl are unsubstituted or substituted with one to three members selected from the group consisting of fluorine, chlorine, bromine, cyano, trifluoromethyl, $(C_1-C_6)$-alkyl, $(C_5-C_{14})$-aryl and $(C_1-C_{14})$-aryl and $(C_1-C_6)$-alkoxy;

$R^2$ is —C(O)$R^4$;

$R^3$ is selected from the group consisting of hydrogen or $(C_1-C_4)$-alkyl;

$R^4$ is selected form the group consisting of hydroxy, $(C_1-C_5)$-alkoxy and N $R^5R^{5'}$;

n is zero or one;

in all their stereoisomeric forms and mixtures thereof in all ratios, and its pharmaceutically acceptable salts.

4. A compound of claim 1, wherein A and B bonded to the thiophene ring in the formula I are hydrogen;

X is selected from the group consisting of $(C_3-C_6)$-alkanediyl, $(C_3-C_6)$-alkenediyl and $(C_3-C_6)$-alkynediyl;

Y is —C(O)$_2$—, or —C(O)—O—;

$R^1$ is selected from the group consisting of $(C_1-C_{18})$-alkyl, $(C_3-C_{14})$-cycloalkyl, $(C_3-C_{14})$-cycloalkyl-$C_1-C_8$)-alkyl, $(C_5-C_{14})$-aryl and $C_5-C_{14}$)-aryl-$C_1-C_8$)-alkyl-, where the alkyl, cycloalkyl and aryl are unsubstituted or substituted with one to three members of the group consisting of fluorine, chlorine, bromine, cyano, trifluoromethyl, $(C_1-C_6)$-alkyl, $(C_5-C_{14})$-aryl and $(C_1-C_6)$-alkoxy;

$R^2$ is —C(O)$R^4$;

$R^3$ is hydrogen;

$R^4$ is hydroxy or $(C_1-C_5)$-alkoxy;

n is one;

in all their stereoisomeric forms and mixtures thereof in all ratios, and its pharmaceutically acceptable salts.

5. A process for the preparation of a compound of claim 1 comprising reacting a compound of formula V with a compound of formula X,

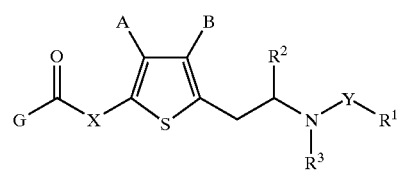

V

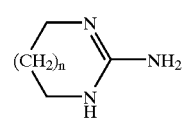

X wherein A, B, X, Y, $R^1$, $R^2$, $R^3$ and n are defined as in claim 1 but wherein functional groups can also be present in the form of precursor groups or can be protected by protective groups, and G is hydroxy or a leaving group.

6. A pharmaceutical composition, comprising a compound of claim 1 and a pharmaceutically acceptable carrier.

7. A method of treating bone disease in warm-blooded animals comprising administering to warm-blooded animals in need thereof an amount of compound of claim 1 sufficient to treat bone disease.

* * * * *